(12) United States Patent
Birch et al.

(10) Patent No.: US 7,169,927 B2
(45) Date of Patent: Jan. 30, 2007

(54) INDOLE-AMIDE DERIVATIVES AND THEIR USE AS GLYCOGEN PHOSPHORYLASE INHIBITORS

(75) Inventors: Alan Martin Birch, Cheshire (GB); Andrew David Morley, Cheshire (GB)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 10/506,748

(22) PCT Filed: Mar. 4, 2003

(86) PCT No.: PCT/GB03/00893

§ 371 (c)(1), (2), (4) Date: Sep. 3, 2004

(87) PCT Pub. No.: WO03/074513

PCT Pub. Date: Sep. 12, 2003

(65) Prior Publication Data

US 2005/0131016 A1    Jun. 16, 2005

(30) Foreign Application Priority Data

Mar. 6, 2002    (GB)    ................... 0205162.1

(51) Int. Cl.
*C07D 215/38*    (2006.01)
*C07D 217/02*    (2006.01)

(52) U.S. Cl. ............... 546/158; 546/144; 546/148; 514/312; 514/311

(58) Field of Classification Search ............ 546/158, 546/144, 148; 514/312, 311
See application file for complete search history.

(56) References Cited

U.S. PATENT DOCUMENTS

| | | |
|---|---|---|
| 3,706,810 A | 12/1972 | Brabander et al. |
| 4,599,198 A | 7/1986 | Hoover |
| 4,668,769 A | 5/1987 | Hoover |
| 4,692,522 A * | 9/1987 | Parsons et al. ............ 540/523 |
| 4,720,503 A | 1/1988 | Witzel |
| 4,751,231 A | 6/1988 | Halczenko |
| 4,786,641 A | 11/1988 | Goldmann |
| 4,794,120 A | 12/1988 | Manoury |
| 5,863,903 A | 1/1999 | Lundgren |
| 5,998,463 A | 12/1999 | Hulin |
| 2004/0002495 A1* | 1/2004 | Sher et al. ............ 514/228.2 |
| 2004/0142938 A1 | 7/2004 | Sher et al. |
| 2004/0220229 A1 | 11/2004 | Bussolotti et al. |
| 2004/0266768 A1 | 12/2004 | Schoenafinger et al. |

FOREIGN PATENT DOCUMENTS

| | | |
|---|---|---|
| DD | 200740 | 6/1983 |
| DE | 4445968 | 6/1996 |
| EP | 697403 | 2/1996 |
| EP | 0846464 | 6/1998 |
| EP | 0884050 | 12/1998 |
| EP | 0978279 | 2/2000 |
| EP | 1149580 | 2/2001 |
| EP | 1177791 | 7/2001 |
| EP | 1125580 | 8/2001 |
| EP | 1134213 | 9/2001 |
| EP | 1136071 | 9/2001 |
| EP | 1 338 594 A1 | 8/2003 |
| EP | 1 340 500 A1 | 9/2003 |
| EP | 1088824 | 1/2004 |

(Continued)

OTHER PUBLICATIONS

Parsons, J Med Chem, vol. 32, pp. 1681-1685, 1989.*

(Continued)

*Primary Examiner*—D. Margaret Seaman

(57) ABSTRACT

Heterocyclic amides of formula (1)

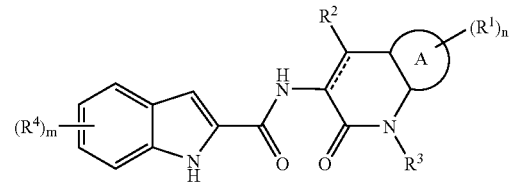

(1)

wherein:

----- is a single or double bond;
A is phenylene or heteroarylene;
m is 0, 1 or 2;
n is 0, 1 or 2;
$R^1$ is selected from for example halo, nitro, cyano, hydroxy, carboxy;
$R^2$ is hydrogen, hydroxy or carboxy;
$R^3$ is selected from for example hydrogen, hydroxy, aryl, heterocyclyl and $C_{1-4}$alkyl(optionally substituted by 1 or 2 $R^8$ groups);
$R^4$ is independently selected from for example hydrogen, halo, nitro, cyano, hydroxy, $C_{1-4}$alkyl, and $C_{1-4}$alkanoyl;
$R^8$ is selected from for example hydroxy, —COCOOR$^9$, —C(O)N(R$^9$)(R$^{10}$), —NHC(O)R$^9$, (R$^9$)(R$^{10}$)N— and —COOR$^9$;
$R^9$ and $R^{10}$ are selected from for example hydrogen, hydroxy, $C_{1-4}$alkyl (optionally substituted by 1 or 2 $R^{13}$);
$R^{13}$ is selected from hydroxy, halo, trihalomethyl and $C_{1-4}$alkoxy;
or a pharmaceutically acceptable salt or pro-drug thereof; possess glycogen phosphorylase inhibitory activity and accordingly have value in the treatment of disease states associated with increased glycogen phosphorylase activity. Processes for the manufacture of said heterocyclic amide derivatives and pharmaceutical compositions containing them are described.

4 Claims, No Drawings

FOREIGN PATENT DOCUMENTS

| | | |
|---|---|---|
| EP | 1145717 | 5/2004 |
| ES | 2081747 | 3/1996 |
| JP | 021247565 | 5/1990 |
| JP | 04179949 | 6/1992 |
| JP | 2001 089368 | 4/2001 |
| JP | 2001 206856 | 7/2001 |
| JP | 2001247565 A | 9/2001 |
| JP | 2004196702 A | 7/2004 |
| WO | WO-93/25574 | 12/1993 |
| WO | WO-95/24391 | 9/1995 |
| WO | WO-96/39384 | 12/1996 |
| WO | WO-96/39385 | 12/1996 |
| WO | WO-97/09040 | 3/1997 |
| WO | WO-97/31901 | 9/1997 |
| WO | WO-97/45425 | 12/1997 |
| WO | WO-98/27108 | 6/1998 |
| WO | WO-98/40353 | 9/1998 |
| WO | WO-98/50359 | 11/1998 |
| WO | WO-99/26659 | 6/1999 |
| WO | WO-99/36393 | 7/1999 |
| WO | WO-00/42213 | 7/2000 |
| WO | WO-00/47206 | 8/2000 |
| WO | WO-01/05954 | 1/2001 |
| WO | WO-01/23347 | 4/2001 |
| WO | 01/32622 A1 | 5/2001 |
| WO | WO-01/32654 | 5/2001 |
| WO | WO-01/52825 | 7/2001 |
| WO | WO-01/68055 | 9/2001 |
| WO | WO-01/68092 | 9/2001 |
| WO | WO-01/68603 | 9/2001 |
| WO | WO-01/94300 | 12/2001 |
| WO | WO-01/96311 | 12/2001 |
| WO | WO-01/96347 | 12/2001 |
| WO | 02/20530 A1 | 3/2002 |
| WO | WO-02/26714 | 4/2002 |
| WO | WO-02/34718 | 5/2002 |
| WO | WO-02/080844 | 10/2002 |
| WO | WO-02/096864 | 12/2002 |
| WO | WO-02/098348 | 12/2002 |
| WO | WO-03/037864 | 5/2003 |
| WO | 03/045920 A1 | 6/2003 |
| WO | 03/072570 A1 | 9/2003 |
| WO | 03/074484 A1 | 9/2003 |
| WO | 03/074485 A2 | 9/2003 |
| WO | 03/074517 A1 | 9/2003 |
| WO | 03/074531 A1 | 9/2003 |
| WO | 03/074532 A1 | 9/2003 |
| WO | 03/091213 A1 | 11/2003 |
| WO | 2004/031193 A1 | 4/2004 |
| WO | 2004/031194 A1 | 4/2004 |
| WO | 2004/041780 A2 | 5/2004 |
| WO | 2004/092158 A1 | 10/2004 |
| WO | 2004113345 A1 | 12/2004 |
| WO | 2005/013975 A1 | 2/2005 |
| WO | 2005/013981 A1 | 2/2005 |
| WO | 2005/018637 A1 | 3/2005 |
| WO | 2005/019172 A1 | 3/2005 |
| WO | 2005/020985 A1 | 3/2005 |
| WO | 2005/020986 A1 | 3/2005 |
| WO | 2005/020987 A1 | 3/2005 |

OTHER PUBLICATIONS

Crochet, R.A., et al., J. Het. Chem., "Synthesis of Substituted Thieno[2,3-b] pyrroles," vol. 11, 143-150 (Apr. 1974).

Teague, J., "Mobilisation of Tissue Glycogen Following Inhibition of Glycogen Phosphorylase in fa/fa Rat," Diabetes, 52, Supp. 2, A365, 1521-P.

Vertigan, H., "Impact of cell glycogen content on modulation of hepatocyte glucose metabolism by pharmacological agents," Diabetologia, 47, Supp. 1, 589, A214.

Font, M. et al. "Indoles and pyridazino[4,5-b]indoles as non-nucleoside analog inhibitors of HIV-1 reverse transcripptase", European Journal Med Chem (1995), 30(12), 963-71.

Lin, T. et al. "Effects of Protein Binding and Experimental Disease States on Brain Uptake of Benzodiazepines in Rats", J Pharmacology & Eptl Therapeutics (1990), 253(1), 45-50.

Varnavas, A. et al. "Quinolone Derivatives: Synthesis and Binding Evaluation on Cholecystokinin Receptors", Farmaco (1996), 51(5), 341-350.

Parsons, W H. et al. "Cholecystokinin Antagonists. Synthesis and Biological Evaluation of 3-Substitued Benzolactams", J Med Chem (1989), 32(8), 1681-5.

Vertigan, H. et al. "Impact of cell glycogen content on modulation of hepatocyte glucose metabolism by pharmacological agents", EASD Munich 2004.

Bartlett, J. et al. "In Vitro and In Vivo Profile of Gpi688, a Novel, Potent Inhibitor of Glycogen Phosphorylase", ADA San Diego 2005.

Green, A R. et al. "The Glycogenic Action of Protein Targeting to Glycogen in Hepatocytes Involves Multiple Mechanisms Including Phosphorylase Inactivation and Glycogen Synthase Translocation", J Biol Chem, 279(45), 46474-46482, 2004.

Roberts, P A. et al. "The temporal relationship between glycogen phosphorylase and activation of the pyruvate dehydrogenase complex during adrenaline infusion in resting canine skeletal muscle", J Physiology-London 545(1), 297-304, 2002.

Simpson, I. et al. "Novel Orally Active Amino-indan Inhibitors of Glycogen Phosphorylase", Cambridge Med Chem Conference, Sep. 2005. Poster EOM.

Birch, A., et al., "Novel Thienopyrrole Glycogen Phosphorylase Inhibitors: In Vitro SAR and Crystallographic Studies," Poster, AstraZeneca UK, CVGI Research, Mereside, Alderley Park, Macclesfield, Cheshire.

Crochet, R.A., et al., "Synthesis of Substituted Thieno[2,3-b] pyrroles," vol. 11, 143-150 (Apr. 1974).

Freeman, S., et al., "Effect of Glucose on Rat and Human Liver Glycogen Phosphorylasea Activity and Potency of a Glycogen Phosphoylase Inhibitor," Diabetes, 52, Supp., 1470-P, A340.

Hartman, G.D., et al., "The Synthesis of 5-Alkylaminomethylthieno[2,3-b]Pyrrole-5-Sulfonamides," Heterocycles, 29(10):1943-1949 (1989).

Hoover, D.J., et al., "Indole-2-carboxamide Inhibitors of Human Liver Glycogen Phosphorylase," J. Med. Chem., 41:2934-2938 (1998).

Hudson, S., et al., "The effect of a glycogen phosphorylase inhibitor upon muscle fatigue in anaesthetised rats," J. Physiol., 539:52-53 (2002).

Jakobsen, P., et al., "Iminosugars: Potential Inhibitors of Liver Glycogen Phosphorylase.," Bioorganic Med. Chem., 9:733-744 (2001).

Martin, W.H., et al., "Discovery of a human liver glycogen phosphorylase inhibitor that lowers blood glucose in vivo," PNAS, 95:1776-1781 (Feb. 1998).

McCormack, J.G., et al., "Pharmacological Approaches to Inhibit Endogenous Glucose Production as a Means of Anti-diabetic Therapy," Curr. Pharmaceutical Design, 7:1451-1474 (2001).

Oikonomakos, N.G., et al., "Allosteric inhibition of glycogen phosphorylase alpha by the potential antidiabetic drug 3-isopropyl 4-(2-chlorophenyl)-1,4-dihydro-1-ethyl-2-methyl-pyridine-3,5,6-tricarboxylate," Protein Sci., 8:1930-1945 (1999).

Rath, V.L. et al., "Activation of Human Liver Glycogen Phosphorylase by Alteration of the Secondary Structure and Packing of the Catalytic Core," Mol. Cell, 6:139-148 (Jul. 2000).

Rosauer, K.G., et al., "Novel, 3,4-Dihydroquinolin-2(1H)-one Inhibitors of Human Glycogen Phosphorylase a," Bioorganic & Medicinal Chemistry Letters, 13:4385-4388 (2003).

Soman, G., et al. "Aromatic Compounds as Allosteric Inhibitors of Glycogen Phosphorylase beta," Biochimica et Biophysica Acta, 358:359-362 (1974).

Soman, G., et al., "The Nature of the Binding Site for Aromatic Compounds in Glycogen Phosphorylase beta," Biochem. J., 147:369-371 (1975).

Teague, J., "Mobilisation of Tissue Glycogen Following Inhibition of Glycogen Phosphorylase in fa/fa Rat," Diabetes, 53, Supp. 1, A365, 1521-P.

Treadway, J.L., et al., "Glycogen phosphorlase inhibitors for treatment of type 2 diabetes mellitus," Exp. Opin. Invest. Drugs, 10(3):439-454 (2001).

Turnbull, A., et al., "Pharmacological Inhibition of Glycogen Phosphorylase (GP) Lowers Plasma Glucose in Rat Models of Type 2 Diabetes," Diabetes, 52, Supp., 1485-P, A343.

Venkatarangan, P., et al., "Prediction of Ligand-REceptor Binding Thermodynamics by Free Energy Force Field Three-Dimensional Quantitative Structure-Activity Relationship Analysis: Applications to a Set of Glucose Analogue Inhibitors of Glycogen Phosphorylase," J. Med. Chem., 42:2169-2179 (1999).

Vertigan, H., "Impact of cell glycogen content on modulation of hepatocyte glucose metabolism by pharmacological agents," Diabetes, 47, Supp., 589, A214.

* cited by examiner

INDOLE-AMIDE DERIVATIVES AND THEIR USE AS GLYCOGEN PHOSPHORYLASE INHIBITORS

This application is a national stage filing under 35 U.S.C. 371 of International Application No. PCT/GB03/00893, filed Mar. 4, 2003, which claims priority from United Kingdom Patent Application No. 0205162.1, filed Mar. 6, 2002, the specification of which is incorporated by reference herein. International Application No. PCT/GB03/00893 was published under PCT Article 21(2) in English.

The present invention relates to heterocyclic amide derivatives, pharmaceutically acceptable salts and in vivo hydrolysable esters thereof. These heterocyclic amides possess glycogen phosphorylase inhibitory activity and accordingly have value in the treatment of disease states associated with increased glycogen phosphorylase activity and thus are potentially useful in methods of treatment of a warm-blooded animal such as man. The invention also relates to processes for the manufacture of said heterocyclic amide derivatives, to pharmaceutical compositions containing them and to their use in the manufacture of medicaments to inhibit glycogen phosphorylase activity in a warm-blooded animal such as man.

The liver is the major organ regulating glycaemia in the post-absorptive state. Additionally, although having a smaller role in the contribution to post-prandial blood glucose levels, the response of the liver to exogenous sources of plasma glucose is key to an ability to maintain euglycaemia. An increased hepatic glucose output (HGO) is considered to play an important role in maintaining the elevated fasting plasma glucose (FPG) levels seen in type 2 diabetics; particularly those with a FPG >140 mg/dl (7.8 mM). (Weyer et al, (1999), J Clin Invest 104: 787–794; Clore & Blackgard (1994), Diabetes 43: 256–262; De Fronzo, R. A., et al, (1992) Diabetes Care 15; 318–355; Reaven, G. M. (1995) Diabetologia 38; 3–13).

Since current oral, anti-diabetic therapies fail to bring FPG levels to within the normal, non-diabetic range and since raised FPG (and glycHbA1c) levels are risk factors for both macro- (Charles, M. A. et al (1996) Lancet 348, 1657–1658; Coutinho, M. et al (1999) Diabetes Care 22; 233–240; Shaw, J. E. et al (2000) Diabetes Care 23, 34–39) and micro-vascular disease (DCCT Research Group (1993) New. Eng. J. Med. 329; 977–986); the reduction and normalisation of elevated FPG levels remains a treatment goal in type 2 DM.

It has been estimated that, after an overnight fast, 74% of HGO was derived from glycogenolysis with the remainder derived from gluconeogenic precursors (Hellerstein et al (1997) Am J Physiol, 272: E163). Glycogen phosphorylase is a key enzyme in the generation by glycogenolysis of glucose-1-phosphate, and hence glucose in liver and also in other tissues such as muscle and neuronal tissue.

Liver glycogen phosphorylase a activity is elevated in diabetic animal models including the db/db mouse and the fa/fa rat (Aiston S et al (2000). Diabetalogia 43, 589–597).

Inhibition of hepatic glycogen phosphorylase with chlor-oindole inhibitors (CP91149 and CP320626) has been shown to reduce both glucagon stimulated glycogenolysis and glucose output in hepatocytes (Hoover et al (1998) J Med Chem 41, 2934–8; Martin et al (1998) PNAS 95, 1776–81). Additionally, plasma glucose concentration is reduced, in a dose related manner, db/db and ob/ob mice following treatment with these compounds.

Studies in conscious dogs with glucagon challenge in the absence and presence of another glycogen phosphorylase inhibitor, Bay K 3401, also show the potential utility of such agents where there is elevated circulating levels of glucagon, as in both Type 1 and Type 2 diabetes. In the presence of Bay R 3401, hepatic glucose output and arterial plasma glucose following a glucagon challenge were reduced significantly (Shiota et al, (1997), Am J Physiol, 273: E868).

The heterocyclic amides of the present invention possess glycogen phosphorylase inhibitory activity and accordingly are expected to be of use in the treatment of type 2 diabetes, insulin resistance, syndrome X, hyperinsulinaemia, hyperglucagonaemia, cardiac ischaemia and obesity, particularly type 2 diabetes.

According to one aspect of the present invention there is provided a compound of formula (1):

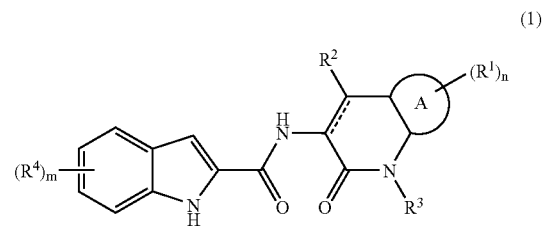

wherein:

===== is a single or double bond;

A is phenylene or heteroarylene;

m is 0, 1 or 2;

n is 0, 1 or 2;

$R^1$ is independently selected from halo, nitro, cyano, hydroxy, carboxy, carbamoyl, N-$C_{1-4}$alkylcarbamoyl, N,N-($C_{1-4}$alkyl)$_2$carbamoyl, sulphamoyl, N-$C_{1-4}$alkylsulphamoyl, N,N-($C_{1-4}$alkyl)$_2$sulphamoyl, —S(O)$_b$$C_{1-4}$alkyl (wherein b is 0, 1, or 2), $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, hydroxy$C_{1-4}$alkyl, fluoromethyl, difluoromethyl, trifluoromethyl and trifluoromethoxy;

or, when n is 2, the two $R^1$ groups, together with the carbon atoms of A to which they are attached, may form a 4 to 7 membered ring, optionally containing 1 or 2 heteroatoms independently selected from O, S and N, and optionally being substituted by one or two methyl groups;

$R^4$ is independently selected from hydrogen, halo, nitro, cyano, hydroxy, fluoromethyl, difluoromethyl, trifluoromethyl, trifluoromethoxy, carboxy, carbamoyl, $C_{1-4}$alkyl, $C_{2-4}$alkenyl, $C_{2-4}$alkynyl, $C_{1-4}$alkoxy and $C_{1-4}$alkanoyl;

$R^2$ is hydrogen, hydroxy or carboxy;

$R^3$ is selected from hydrogen, hydroxy, $C_{1-4}$alkoxy, $C_{1-4}$alkanoyl, carbamoyl, $C_{3-7}$cycloalkyl (optionally substituted with 1 or 2 hydroxy groups), cyano($C_{1-4}$)alkyl, aryl, heterocyclyl, $C_{1-4}$alkyl (optionally substituted by 1 or 2 $R^8$ groups), and groups of the formulae B and B':

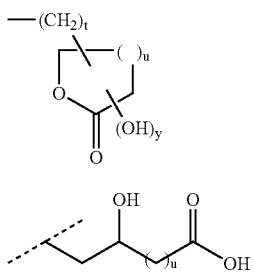

(B)

(B')

wherein y is 0 or 1, t is 0, 1, 2 or 3 and u is 1 or 2; provided that the hydroxy group is not a substituent on the ring carbon adjacent to the ring oxygen;

$R^8$ is independently selected from hydroxy, $C_4$alkoxy$C_{1-4}$alkoxy, hydroxy$C_{1-4}$alkoxy, 5- and 6-membered cyclic acetals and mono- and di-methyl derivatives thereof, aryl, heterocyclyl, $C_{3-7}$cycloalkyl, $C_{1-4}$alkanoyl, $C_{1-4}$alkoxy, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), —N(OH)CHO, —C(=N—OH)NH$_2$, —C(=N—OH)NHC$_{1-4}$alkyl, —C(=N—OH)N(C$_{1-4}$alkyl)$_2$, —C(=N—OH)NHC$_{3-6}$cycloalkyl, —C(=N—OH)N(C$_{3-6}$cycloalkyl)$_2$, —COCOOR$^9$, —C(O)N(R$^9$)(R$^{10}$), —NHC(O)R$^9$, —C(O)NHSO$_2$(C$_{1-4}$alkyl), —NHSO$_2$R$^9$, (R$^9$)(R$^{10}$)NSO$_2$—, —COCH$_2$OR$^{11}$, (R$^9$)(R$^{10}$)N— and —COOR$^9$;

$R^9$ and $R^{10}$ are independently selected from hydrogen, hydroxy, $C_{1-4}$alkyl (optionally substituted by 1 or 2 $R^{13}$), $C_{3-7}$cycloalkyl (optionally substituted by 1 or 2 hydroxy groups), cyano($C_{1-4}$)alkyl, trihalo($C_{1-4}$)alkyl, aryl, heterocyclyl and heterocyclyl($C_{1-4}$alkyl); or $R^9$ and $R^{10}$ together with the nitrogen to which they are attached form a 4- to 6-membered ring where the ring is optionally substituted on carbon by 1 or 2 substituents independently selected from oxo, hydroxy, carboxy, halo, nitro, cyano, carbonyl, $C_{1-4}$alkoxy and heterocyclyl; or the ring may be optionally substituted on two adjacent carbons by —O—CH$_2$—O— to form a cyclic acetal wherein one or both of the hydrogens of the —O—CH$_2$—O— group may be replaced by a methyl;

$R^{13}$ is selected from hydroxy, halo, trihalomethyl and $C_{1-4}$alkoxy;

$R^{11}$ is independently selected from hydrogen, $C_{1-4}$alkyl and hydroxy$C_{1-4}$alkyl;

or a pharmaceutically acceptable salt or pro-drug thereof.

In another aspect of the present invention there is provided a compound of formula (1):

wherein:

----- is a single or double bond;
A is phenylene or heteroarylene;
m is 0, 1 or 2;
n is 0, 1 or 2;

wherein $R^1$ is independently selected from hydrogen, halo, nitro, cyano, hydroxy, amino, carboxy, carbamoyl, N-C$_{1-4}$alkylcarbamoyl, N,N-(C$_{1-4}$alkyl)$_2$carbamoyl, sulphamoyl,
N-C$_{1-4}$alkylsulphamoyl, N,N-(C$_{1-4}$alkyl)$_2$sulphamoyl, sulfino, sulfo, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N-(C$_{1-4}$alkyl)amino, N,N-(C$_{1-4}$alkyl)$_2$amino, hydroxyC$_{1-4}$ alkyl, fluoromethyl, difluoromethyl, trifluoromethyl, trifluoromethoxy, C$_{1-4}$alkoxy and $R^1$ is of the formula A' or A":

(A')

—CH$_2$CH(OH)(CH$_2$)$_u$CO$_2$H (A")

wherein x is 0 or 1, r is 0, 1, 2 or 3 and s is 1 or 2; provided that the hydroxy group is not a substituent on the ring carbon adjacent to the ring oxygen;

wherein $R^4$ is independently selected from hydrogen, halo, nitro, cyano, hydroxy, amino, carboxy, carbamoyl, N-C$_{1-4}$alkylcarbamoyl, N,N-(C$_{1-4}$alkyl)$_2$carbamoyl, sulphamoyl,
N-C$_{1-4}$alkylsulphamoyl, N,N-(C$_{1-4}$alkyl)$_2$sulphamoyl, sulfino, sulfo, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N-(C$_{1-4}$yl)amino, N,N-(C$_{1-4}$alkyl)$_2$amino, hydroxyC$_{1-4}$ alkyl, fluoromethyl, difluoromethyl, trifluoromethyl and trifluoromethoxy;

$R^2$ is hydrogen, hydroxy or carboxy;

$R^3$ is selected from hydrogen, hydroxy, $C_{1-4}$alkanoyl, carbamoyl, $C_{1-4}$alkyl (optionally substituted by 1 or 2 hydroxy groups provided that when there are 2 hydroxy groups they are not substituents on the same carbon), $C_{5-7}$cycloalkyl (optionally substituted with 1 or 2 hydroxy groups provided that when there are 2 hydroxy groups they are not substituents on the same carbon), cyano($C_{1-4}$)alkyl, 4-butanolidyl, 5-pentanolidyl, tetrahydrothiopyranyl, 1-oxotetrahydrothiopyranyl, 1,1-dioxotetrahydrothiopyranyl, $C_{1-4}$alkyl [substituted by 1 or 2 $R^8$ groups (provided that when there are 2 $R^8$ groups they are not substituents on the same carbon)] and groups of the formulae B and B':

(B)

—CH$_2$CH(OH)(CH$_2$)$_u$CO$_2$H (B')

wherein y is 0 or 1, t is 0, 1, 2 or 3 and u is 1 or 2; provided that the hydroxy group is not a substituent on the ring carbon adjacent to the ring oxygen);

{wherein $R^8$ is independently selected from hydroxy, $C_{1-4}$alkoxy$C_{1-4}$alkoxy, hydroxy$C_{1-4}$alkoxy, 2,2-dimethyl-1,3-dioxolan-4-yl, heterocyclyl, $C_{1-4}$alkanoyl, $C_{1-4}$alkoxy, $C_{1-4}$alkanesulfinyl, $C_{1-4}$alkanesulfonyl, —N(OH)CHO, —COCOOR$^9$, $(R^9)(R^{10})$NCO—, $(R^9)(R^{10})$NSO$_2$—, —COCH$_2$OR$^{11}$, $(R^9)(R^{10})$N— and —COOR$^9$;

[wherein $R^9$ and $R^{10}$ are independently selected from hydrogen, hydroxy, $C_{1-4}$alkyl (optionally substituted by 1 or 2 hydroxy groups provided that when there are 2 hydroxy groups they are not substituents on the same carbon), $C_{5-7}$cycloalkyl (optionally substituted by 1 or 2 hydroxy groups provided that when there are 2 hydroxy groups they are not substituents on the same carbon), cyano($C_{1-4}$)alkyl, 4-butanolidyl, 5-pentanolidyl, tetrahydrothiopyranyl, 1-oxotetrahydrothiopyranyl g, 1,1-dioxotetrahydrothiopyranyl, 2,2-dimethyl-1,3-dioxolan-4-yl and $C_{1-4}$alkyl substituted by $R^{13}$;

(wherein $R^{13}$ is selected from hydroxy, $C_{1-4}$alkoxy, heterocyclyl, $C_{1-4}$alkanoyl, $C_{1-4}$alkanesulfinyl, $C_{1-4}$alkanesulfonyl, —N(OH)CHO, $(R^{11})(R^{12})$NCO—, $(R^{11})(R^{12})$NSO$_2$—, —COCH$_2$OR$^{11}$, $(R^{11})(R^{12})$N—;

{wherein $R^{11}$ and $R^{12}$ are independently selected from hydrogen, $C_{1-4}$alkyl, $C_{1-4}$alkoxy, hydroxy$C_{1-4}$alkyl, $C_{1-4}$alkylS(O)$_b$ (wherein b is 0, 1 or 2)}); and $R^9$ and $R^{10}$ can together with the nitrogen to which they are attached form 4- to 6-membered ring where the ring is optionally substituted on carbon by 1 or 2 substituents selected from oxo, hydroxy, carboxy, halo, nitro, nitroso, cyano, isocyano, amino, N-$C_{1-4}$alkylamino, N,N-$(C_{1-4})_2$alkylamino, carbonyl, sulfo, $C_{1-4}$alkoxy, heterocyclyl, $C_{1-4}$alkanoyl, $C_{1-4}$alkanesulfinyl, $C_{1-4}$alkanesulfonyl, —N(OH)CHO, $(R^{11})(R^{12})$NCO—, $(R^{11})(R^{12})$NSO$_2$—, —COCH$_2$OR$^{11}$, $(R^{11})(R^{12})$N—;

wherein $R^{11}$ and $R^{12}$ are as defined above]};

provided that when $R^1$ is of the formula A' or A" then $R^3$ does not contain a group of the formula B or B' and when $R^3$ is of the formula B or B' then $R^1$ does not contain a group of the formula A' or A";

or a pharmaceutically acceptable salt or in vivo hydrolysable ester thereof.

It is to be understood that when A is heteroarylene, the bridgehead atoms joining ring A to the piperidinone ring may be heteroatoms. Therefore, for example, the definition of

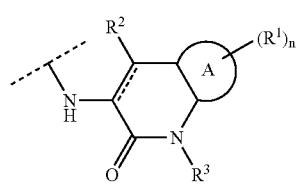

when A is heteroarylene encompasses the structures

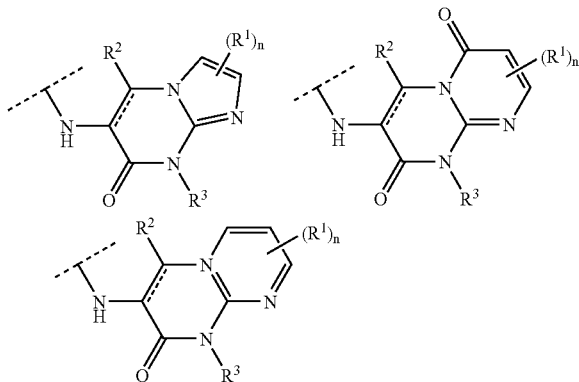

It is to be understood that, where optional substitution on alkyl or cycloalkyl groups in $R^3$, $R^9$ and $R^{10}$ (as defined hereinbefore or hereinafter) allows two hydroxy substituents on the alkyl or cycloalkyl group, or one hydroxy substituent and a second substituent linked by a heteroatom (for example alkoxy), then these two substituents are not substituents on the same carbon atom of the alkyl or cycloalkyl group.

In another aspect, the invention relates to compounds of formula (1) as hereinabove defined or to a pharmaceutically acceptable salt.

In another aspect, the invention relates to compounds of formula (1) as hereinabove defined or to a pro-drug thereof. Suitable examples of pro-drugs of compounds of formula (1) are in-vivo hydrolysable esters of compounds of formula (1). Therefore in another aspect, the invention relates to compounds of formula (1) as hereinabove defined or to an in-vivo hydrolysable ester thereof.

It is to be understood that, insofar as certain of the compounds of formula (1) defined above may exist in optically active or racemic forms by virtue of one or more asymmetric carbon atoms, the invention includes in its definition any such optically active or racemic form which possesses glycogen phosphorylase inhibition activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Within the present invention it is to be understood that a compound of the formula (1) or a salt thereof may exhibit the phenomenon of tautomerism and that the formulae drawings within this specification can represent only one of the possible tautomeric forms. It is to be understood that the invention encompasses any tautomeric form which has glycogen phosphorylase inhibition activity and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It is also to be understood that certain compounds of the formula (1) and salts thereof can exist in solvated as well as unsolvated forms such as, for example, hydrated forms. It is to be understood that the invention encompasses all such solvated forms which have glycogen phosphorylase inhibition activity.

It is also to be understood that certain compounds of the formula (1) may exhibit polymorphism, and that the invention encompasses all such forms which possess glycogen phosphorylase inhibition activity.

The present invention relates to the compounds of formula (1) as hereinbefore defined as well as to the salts thereof. Salts for use in pharmaceutical compositions will be pharmaceutically acceptable salts, but other salts may be useful in the production of the compounds of formula (1) and their pharmaceutically acceptable salts. Pharmaceutically acceptable salts of the invention may, for example, include acid addition salts of the compounds of formula (1) as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromides, phosphates, sulphates, hydrogen sulphates, alkylsulphonates, arylsulphonates, acetates, benzoates, citrates, maleates, fumarates, succinates, lactates and tartrates. In addition where the compounds of formula (1) are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

The compounds of the invention may be administered in the form of a pro-drug which is broken down in the human or animal body to give a compound of the invention. A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the invention or a pharmaceutically-acceptable salt thereof.

Various forms of prodrugs are known in the art, for examples see:
a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem Pharm Bull, 32, 692 (1984).

An in vivo hydrolysable ester of a compound of formula (1) containing carboxy or hydroxy group is, for example. A pharmaceutically acceptable ester which is cleaved in the human or animal body to produce the parent acid or alcohol.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable pharmaceutically-acceptable esters for hydroxy include inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include $C_{1-10}$alkanoyl, for example acetyl; benzoyl; phenylacetyl; substituted benzoyl and phenylacetyl, $C_{1-10}$alkoxycarbonyl (to give alkyl carbonate esters), for example ethoxycarbonyl; di-$(C_{1-4})$alkylcarbamoyl and N-(di-$(C_{1-4})$alkylaminoethyl)-N-$(C_{1-4})$alkylcarbamoyl (to give carbamates); di-$(C_{1-4})$alkylaminoacetyl and carboxyacetyl. Examples of ring substituents on phenylacetyl and benzoyl include aminomethyl, $(C_{1-4})$alkylaminomethyl and di-$((C_{1-4})$alkyl)aminomethyl, and morpholino or piperazino linked from a ring nitrogen atom via a methylene linking group to the 3- or 4-position of the benzoyl ring. Other interesting in-vivo hyrolysable esters include, for example, $R^A C(O)O(C_{1-6})$alkyl-CO—, wherein $R^A$ is for example, benzyloxy-$(C_{1-4})$alkyl, or phenyl). Suitable substituents on a phenyl group in such esters include, for example, 4-$(C_{1-4})$piperazino-$(C_{1-4})$alkyl, piperazino-$(C_{1-4})$alkyl and morpholino-$(C_1$—$C_4)$alkyl.

In this specification the generic term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "$C_{1-4}$alkyl" includes methyl, ethyl, propyl, isopropyl and t-butyl. An analogous convention applies to other generic terms, for example "$C_{2-4}$alkenyl" includes vinyl, allyl and 1-propenyl and "$C_{2-4}$alkynyl" includes ethynyl, 1-propynyl and 2-propynyl.

The term "hydroxy$C_{1-4}$alkyl" includes hydroxymethyl, hydroxyethyl, hydroxypropyl, hydroxyisopropyl and hydroxybutyl. The term "hydroxyethyl" includes 1-hydroxyethyl and 2-hydroxyethyl. The term "hydroxypropyl" includes 1-hydroxypropyl, 2-hydroxypropyl and 3-hydroxypropyl and an analogous convention applies to terms such as hydroxybutyl. The term "dihydroxy$C_{1-4}$alkyl" includes dihydroxyethyl, dihydroxypropyl, dihydroxyisopropyl and dihydroxybutyl. The term "dihydroxypropyl" includes 1,2-dihydroxypropyl and 1,3-dihydroxypropyl. An analogous convention applies to terms such as dihydroxyisopropyl and dihydroxybutyl.

The term "halo" refers to fluoro, chloro, bromo and iodo. The term "dihalo$C_{1-4}$alkyl" includes difluoromethyl and dichloromethyl. The term "trihalo$C_{1-4}$alkyl" includes trifluoromethyl.

Examples of "5- and 6-membered cyclic acetals and mono- and di-methyl derivatives thereof" are:
1,3-dioxolan-4-yl, 2-methyl-1,3-dioxolan-4-yl, 2,2-dimethyl-1,3-dioxolan-4-yl; 2,2-dimethyl-1,3-dioxan-4-yl; 2,2-dimethyl-1,3-dioxan-5-yl; 1,3-dioxan-2-yl.

Examples of "$C_{1-4}$alkoxy" include methoxy, ethoxy, propoxy and isopropoxy. Examples of "$C_{1-6}$alkoxy" include the examples of "$C_{1-4}$alkoxy" and additionally butyloxy, t-butyloxy, pentoxy and 1,2-(methyl)$_2$propoxy. Examples of "$C_{1-4}$alkanoyl" include formyl, acetyl and propionyl. Examples of "$C_{1-6}$alkanoyl" include the example of "$C_{1-4}$alkanoyl" and additionally butanoyl, pentanoyl, hexanoyl and 1,2-(methyl)$_2$propionyl. Examples of "$C_{1-4}$alkanoyloxy" are formyloxy, acetoxy and propionoxy. Examples of "$C_{1-6}$alkanoyloxy" include the examples of "$C_{1-4}$alkanoyloxy" and additionally butanoyloxy, pentanoyloxy, hexanoyloxy and 1,2-(methyl)$_2$propionyloxy. Examples of "N-($C_{1-4}$alkyl)amino" include methylamino and ethylamino. Examples of "N,N-($C_{1-4}$alkyl)$_2$amino" include N-N-(methyl)$_2$amino, N-N-(ethyl)$_2$amino and N-ethyl-N-methylamino. Examples of "N-($C_{1-4}$alkyl)carbamoyl" are methylcarbamoyl and ethylcarbamoyl. Examples of "N,N-($C_{1-4}$alkyl)$_2$carbamoyl" are N,N-(methyl)$_2$carbamoyl, N,N-(ethyl)$_2$carbamoyl and N-methyl-N-ethylcarbamoyl. Examples of "N-($C_{1-4}$alkyl)sulphamoyl" are N-(methyl)sulphamoyl and N-(ethyl)sulphamoyl. Examples of "N,N-($C_{1-4}$alkyl)$_2$sulphamoyl" are N,N-(methyl)$_2$sulphamoyl, N,N-(ethyl)$_2$sulphamoyl and N-(methyl)-N-(ethyl)sulphamoyl.

Examples of "$C_{1-4}$alkoxy$C_{1-4}$alkoxy" are methoxymethoxy, ethoxymethoxy, ethoxyethoxy and methoxyethoxy. Examples of "hydroxy$C_{1-4}$alkoxy" are hydroxyethoxy and hydroxypropoxy. Examples of "hydroxypropoxy" are 1-hydroxypropoxy, 2-hydroxypropoxy and 3-hydroxypropoxy.

Examples of "cyano($C_{1-4}$)alkyl" are cyanomethyl, cyanoethyl and cyanopropyl. Examples of "$C_{5-7}$cycloalkyl" are cyclopentyl, cyclohexyl and cycloheptyl. Examples of "$C_{3-8}$cycloalkyl" and "$C_{3-7}$cycloalkyl" include "$C_{5-7}$cycloalkyl", cyclopropyl, cyclobutyl and cyclooctyl. Examples of "$C_{3-6}$cycloalkyl" inclulde cyclopropyl, cyclobutyl, cyclopentyl and cyclohexyl.

The term "amino$C_{1-4}$alkyl" includes aminomethyl, aminoethyl, aminopropyl, aminoisopropyl and aminobutyl. The term "aminoethyl" includes 1-aminoethyl and 2-aminoethyl. The term "aminopropyl" includes 1-aminopropyl, 2-aminopropyl and 3-aminopropyl and an analogous convention applies to terms such as aminoethyl and aminobutyl.

The term "sulfo" means $HOSO_2$—. The term "sulfino" means $HO_2S$—.

Examples of "$C_{1-4}$alkylS(O)$_b$ (wherein b is 0, 1 or 2)" include methylthio, ethylthio, propylthio, methanesulphinyl, ethanesulphinyl, propanesulphinyl, mesyl, ethanesulphonyl, propanesulphonyl and isopropanesulphonyl.

Examples of "$C_{3-6}$cycloalkylS(O)$_b$ (wherein b is 0, 1 or 2)" include cyclopropylthio, cyclopropylsulphinyl, cyclopropylsulphonyl, cyclobutylthio, cyclobutylsulphinyl, cyclobutylsulphonyl, cyclopentylthio, cyclopentylsulphinyl and cyclopentylsulphonyl.

Examples of "arylS(O)$_b$ (wherein b is 0, 1 or 2)" include phenylthio, phenylsulphinyl and phenylsulfonyl. Examples of "benzylS(O)$_b$ (wherein b is 0, 1 or 2)" inculde benzylthio, benzylsulfinyl and benzylsulfonyl. Examples of "heterocyclylS(O)$_b$ (wherein b is 0, 1 or 2)" include pyridylthio, pyridylsulfinyl, pyridylsulfonyl, imidazolylthio, imidazolylsulfinyl, imidazolylsulfonyl, pyrimidinylthio, pyrimidinylsufinyl, pyrimidinylsulfonyl, piperidylthio, piperidylsulfinyl and piperidylsulfonyl.

Where optional substituents are chosen from "0, 1, 2 or 3" groups it is to be understood that this definition includes all substituents being chosen from one of the specified groups or the substituents being chosen from two or more of the specified groups. An analogous convention applies to substituents chose from "0, 1 or 2" groups and "1 or 2" groups.

"Heterocyclyl" is a saturated, partially saturated or unsaturated, optionally substituted monocyclic ring containing 5 to 7 atoms of which 1, 2, 3 or 4 ring atoms are chosen from nitrogen, sulphur or oxygen, which may, unless otherwise specified, be carbon or nitrogen linked, wherein a —$CH_2$— group can optionally be replaced by a —C(O)— and a ring sulphur atom may be optionally oxidised to form the S-oxide(s). Examples and suitable values of the term "heterocyclyl" are morpholino, morpholinyl, piperidino, piperidyl, pyridyl, pyranyl, pyrrolyl, imidazolyl, thiazolyl, thienyl, dioxolanyl, thiadiazolyl, piperazinyl, isothiazolidinyl, triazolyl, tetrazolyl, pyrrolidinyl, 2-oxazolidinonyl, 5-isoxazolonyl, thiomorpholino, pyrrolinyl, homopiperazinyl, 3,5-dioxapiperidinyl, 3-oxopyrazolin-5-yl, tetrahydropyranyl, tetrahydrothiopyranyl, 1-oxotetrahydrothiopyranyl, 1,1-dioxotetrahydrothiopyranyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, and oxadiazolyl.

Suitably a "heterocyclyl" is morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, and 1,2,4-oxadiazolyl.

Conveniently "heterocyclyl" is oxazolyl, 1,3,4-oxadiazolyl, 1,2,4-oxadiazolyl, tetrazolyl, thizoyl, thiadiazolyl, pyridyl, imidazolyl, furyl, thienyl, morpholine, pyrimidyl, pyrazinyl, pyridazinyl, pyrazolyl, pyrazolinyl, and piperazinyl.

Suitable optional substituents for "heterocyclyl" as a saturated or partially saturated ring are 1, 2 or 3 substituents independently selected from halo, cyano, hydroxy, $C_{1-4}$alkyl, $C_{1-4}$alkoxy and $C_{1-4}$alkylS(O)$_b$ (wherein b is 0, 1 or 2). Further suitable substituents for "heterocyclyl" as a saturated or partially saturated ring are 1, 2 or 3 substituents independently selected from fluoro, chloro, cyano, hydroxy, methyl, ethyl, methoxy, methylthio, methylsulfinyl and methylsulfonyl.

Suitable optional susbtituents for "heterocyclyl" as an unsaturated ring are 1, 2 or 3 substituents independently selected from halo, cyano, nitro, amino, hydroxy, $C_{1-4}$alkyl, $C_{1-4}$alkoxy, $C_{1-4}$alkylS(O)$_b$ (wherein b is 0, 1 or 2), N-($C_{1-4}$alkyl)amino and N,N-($C_{1-4}$alkyl)$_2$amino. Further suitable optional susbtituents for "heterocyclyl" as an unsaturated ring are 1, 2 or 3 substituents independently selected from fluoro, chloro, cyano, nitro, amino, methylamino, dimethylamino, hydroxy, methyl, ethyl, methoxy, methylthio, methylsulfinyl and methylsulfonyl.

Examples of "(heterocyclyl)$C_{1-4}$alkyl" are morpholinomethyl, morpholinethyl, morpholinylmethyl, morpholinylethyl, piperidinomethyl, piperidinoethyl, piperidylmethyl, piperidylethyl, imidazolylmethyl, imidazolylethyl, oxazolylmethyl, oxazolylethyl, 1,3,4-oxadiazolylmethyl, 1,2,4-oxadiazolylmethyl, 1,2,4-oxadiazolylethyl, pyridylmethyl, pyridylethyl, furylmethyl, furylethyl, (thienyl)methyl, (thienyl)ethyl, pyrazinylmethyl, pyrazinylethyl, piperazinylmethyl and piperazinylethyl.

Examples of "aryl" are optionally substituted phenyl and naphthyl.

Examples of "aryl($C_{1-4}$)alkyl" are benzyl, phenethyl, naphthylmethyl and naphthylethyl.

Suitable optional substituents for "aryl" groups are 1, 2 or 3 substituents independently selected from halo, cyano, nitro, amino, hydroxy, $C_{1-4}$alkyl, $C_{1-4}$alkoxy, $C_{1-4}$alkylS(O)$_b$ (wherein b is 0, 1 or 2), N-($C_{1-4}$alkyl)amino and N,N-($C_{1-4}$ alkyl)$_2$amino. Further suitable optional susbtituents for "aryl" groups are 1, 2 or 3 substituents independently selected from fluoro, chloro, cyano, nitro, amino, methylamino, dimethylamino, hydroxy, methyl, ethyl, methoxy, methylthio, methylsulfinyl and methylsulfonyl.

"Heteroarylene" is a diradical of a heteroaryl group. A heteroaryl group is an aryl, monocyclic ring containing 5 to 7 atoms of which 1, 2, 3 or 4 ring atoms are chosen from nitrogen, sulphur or oxygen. Examples of heteroarylene are oxazolylene, oxadiazolylene, pyridylene, pyrimidinylene, imidazolylene, triazolylene, tetrazolylene, pyrazinylene, pyridazinylene, pyrrolylene, thienylene and furylene.

Suitable optional substituents for heteroaryl groups, unless otherwise defined, are 1, 2 or 3 substituents independently selected from halo, cyano, nitro, amino, hydroxy, $C_{1-4}$alkyl, $C_{1-4}$alkoxy, $C_{1-4}$alkylS(O)$_b$ (wherein b is 0, 1 or 2), N-($C_{1-4}$alkyl)amino and N,N-($C_{1-4}$alkyl)$_2$amino. Further suitable optional susbtituents for "heteroaryl" groups are 1, 2 or 3 substituents independently selected from fluoro, chloro, cyano, nitro, amino, methylamino, dimethylamino, hydroxy, methyl, ethyl, methoxy, methylthio, methylsulfinyl and methylsulfonyl.

Preferred values of A, $R^1$, $R^2$, $R^3$, $R^4$, m and n are as follows. Such values may be used where appropriate with any of the definitions, claims, aspects or embodiments defined hereinbefore or hereinafter.

In one embodiment of the invention are provided compounds of formula (1), in an alternative embodiment are provided pharmaceutically-acceptable salts of compounds of formula (1), in a further alternative embodiment are provided in-vivo hydrolysable esters of compounds of formula (1), and in a further alternative embodiment are provided pharmaceutically-acceptable salts of in-vivo hydrolysable esters of compounds of formula (1).

In one aspect of the present invention m is 1 or 2.

In another aspect of the invention m is 1.

In one aspect of the present invention $R^4$ is selected from hydrogen, halo, cyano, hydroxy, fluoromethyl, difluoromethyl and trifluoromethyl.

In another aspect of the invention $R^4$ is hydrogen or halo.

Preferably $R^4$ is selected from hydrogen, chloro or bromo.

More preferably $R^4$ is chloro.

In one aspect of the invention A is phenylene.

In another aspect of the invention A is heteroarylene.

Preferably A is selected from phenylene, pyridylene, pyrimidinylene, pyrrolylene, imidazolylene, triazolylene, tetrazolylene, oxazolylene, oxadiazolylene, thienylene and furylene.

In one aspect of the invention n is 0 or 1.

In one aspect preferably n is 1.

In another, preferably n is 0.

When n is 2, and the two $R^1$ groups, together with the carbon atoms of A to which they are attached, form a 4 to 7 membered ring, optionally containing 1 or 2 heteroatoms independently selected from O, S and N, conveniently such a ring is a 5 or 6 membered ring containing two O atoms (ie a cyclic acetal). When the two $R^1$ groups together form such a cyclic acetal, preferably it is not substituted. Most preferably the two $R^1$ groups together are the group —O—CH$_2$—O—.

In another aspect of the present invention $R^1$ is selected from halo, nitro, cyano, hydroxy, fluoromethyl, difluoromethyl, trifluoromethyl and $C_{1-4}$alkoxy.

In a further aspect $R^1$ is selected from halo, nitro, cyano, hydroxy, fluoromethyl, difluoromethyl, trifluoromethyl, —S(O)$_b$C$_{1-4}$alkyl (wherein b is 0, 1 or 2), $C_{1-4}$alkyl and $C_{1-4}$alkoxy.

In a further aspect $R^1$ is selected from halo, nitro, cyano, hydroxy, fluoromethyl, difluoromethyl, trifluoromethyl, —S(O)$_b$Me (wherein b is 0, 1 or 2), methyl and methoxy.

In a further aspect, $R^1$ is $C_{1-4}$alkyl.

Preferably $R^1$ is selected from halo and $C_{1-4}$alkoxy.

In another embodiment preferably $R^1$ is selected from fluoro, chloro, methyl, ethyl, methoxy and O—CH$_2$—O—.

In one aspect of the invention

----- is a single bond.

In another aspect of the invention

----- is a double bond.

In one aspect of the invention $R^2$ is hydrogen.

In another aspect of the invention $R^2$ is carboxy.

In another aspect of the invention $R^2$ is hydroxy.

Preferably $R^2$ is hydrogen.

Suitable values for $R^3$ as heterocyclyl are morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, and 1,2,4-oxadiazolyl, tetrahydrothiopyranyl, 1-oxotetrahydrothiopyranyl, 1,1-dioxotetrahydrothiopyranyl.

More suitable values for $R^3$ as heterocyclyl are pyridyl, pyrimidinyl and imidazolyl.

Further suitable values for $R^3$ as heterocyclyl are tetrahydrothiopyranyl, 1-oxotetrahydrothiopyranyl, 1,1-dioxotetrahydrothiopyranyl.

In one aspect of the invention $R^3$ is selected from hydrogen, hydroxy, $C_{1-4}$alkoxy, $C_{1-4}$alkanoyl, carbamoyl, $C_{3-7}$cycloalkyl (optionally substituted with 1 or 2 hydroxy groups, cyano($C_{1-4}$)alkyl, phenyl, morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, and 1,2,4-oxadiazolyl, tetrahydrothiopyranyl, 1-oxotetrahydrothiopyranyl, 1,1-dioxotetrahydrothiopyranyl and $C_{1-4}$alkyl (optionally substituted by 1 or 2 $R^8$ groups);

$R^9$ and $R^{10}$ are independently selected from hydrogen, hydroxy, $C_{1-4}$alkyl (optionally substituted by 1 or 2 $R^{13}$ groups), $C_{3-7}$cycloalkyl (optionally substituted by 1 or 2 hydroxy groups), cyano($C_{1-4}$)alkyl, trihalo $C_{1-4}$alkyl, aryl, heterocyclyl and heterocyclyl($C_{1-4}$alkyl);

or $R^9$ and $R^{10}$ together with the nitrogen to which they are attached form a 4- to 6-membered ring where the ring is optionally substituted on carbon by 1 or 2 substituents selected from oxo, hydroxy, carboxy, halo, nitro, cyano, carbonyl and $C_{1-4}$alkoxy, or the ring may be optionally substituted on two adjacent carbons by —O—CH$_2$—O— to form a cyclic acetal wherein one or both of the hydrogens of the —O—CH$_2$—O— group may be replaced by a methyl;

$R^8$ is independently selected from hydroxy, $C_{1-4}$alkoxy$C_{1-4}$ alkoxy, hydroxy$C_{1-4}$alkoxy, 5- and 6-membered cyclic acetals and mono- and di-methyl derivatives thereof, aryl, heterocyclyl, $C_{3-7}$cycloalkyl, $C_{1-4}$alkanoyl, $C_{1-4}$alkoxy, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), —N(OH)CHO, —C(=N—OH)NH$_2$, —C(=N—OH)NHC$_{1-4}$alkyl, —C(=N—OH)N(C$_{1-4}$alkyl)$_2$, —C(=N—OH)NHC$_{3-6}$cycloalkyl, —C(=N—OH)N(C$_{3-6}$cycloalkyl)$_2$, —COCOOR$^9$, —C(O)N(R$^9$)(R$^{10}$), —NHC(O)R$^9$, —C(O)NHSO$_2$(C$_{1-4}$alkyl), —NHSO$_2$R$^9$, (R$^9$)(R$^{10}$)NSO$_2$—, —COCH$_2$OR$^{11}$, (R$^9$)(R$^{10}$)N— and —COOR$^9$;

$R^{13}$ is selected from hydroxy, halo, trifluoromethyl and $C_{1-4}$alkoxy;

$R^{11}$ is selected from hydrogen, $C_{1-4}$alkyl and hydroxy$C_{1-4}$alkyl.

In a further aspect of the invention $R^3$ is selected from cyano$C_{1-4}$alkyl and $C_{1-4}$alkyl (optionally substituted by 1 or 2 of $R^8$ groups);

$R^8$ is independently selected from hydroxy, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, $C_{1-4}$alkoxy, $C_{1-4}$alkanoyl, $C_{1-4}$alkylS(O)$_b$— (wherein b is 0, 1 or 2), —C(O)N(R$^9$)(R$^{10}$), —COOR$^9$, —C(O)NHSO$_2$Me, —C(=N—OH)NH$_2$, —C(=N—OH)NHC$_{1-4}$alkyl, —C(=N—OH)N(C$_{1-4}$alkyl)$_2$ and —NHSO$_2$R$^9$;

$R^9$ and $R^{10}$ are independently selected from hydrogen, hydroxy, $C_{1-4}$alkyl optionally substituted with $R^{13}$ (wherein $R^{13}$ is $C_{1-4}$alkoxy or hydroxy); or $R^9$ and $R^{10}$ together with the nitrogen to which they are attached form a 4- to 6-membered ring where the ring may be optionally substituted on carbon by 1 or 2 hydroxy groups or carboxy groups), or the ring may be optionally substituted on two adjacent carbons by —O—CH$_2$—O— to form a cyclic acetal wherein one or both of the hydrogens of the —O—CH$_2$—O— group may be replaced by a methyl.

In a further aspect of the invention $R^3$ is selected from cyano$C_{1-4}$alkyl and $C_{1-4}$alkyl (optionally substituted by 1 or 2 $R^8$ groups);

wherein $R^8$ is independently selected from hydroxy, 2,2-dimethyl-1,3-dioxolan-4-yl, 1,2,4-oxadiazolyl, 1,3,4-oxadiazolyl, tetrazolyl, $C_{1-4}$alkoxy, $C_{1-4}$alkanoyl, $C_{1-4}$alkylS(O)$_b$— (wherein b is 0, 1 or 2), —C(O)N(R$^9$)(R$^{10}$), —COOR$^9$, —C(O)NHSO$_2$Me, —C(=N—OH)NH$_2$;

wherein $R^9$ and $R^{10}$ are independently selected from hydrogen, hydroxy, $C_{1-4}$alkyl optionally substituted with $R^{13}$ (wherein $R^{13}$ is $C_{1-4}$alkoxy or hydroxy); or $R^9$ and $R^{10}$ together with the nitrogen to which they are attached form a 4- to 6-membered ring selected from piperidine, 4-hydroxy piperidine, pyrrolidine, 3,4-dihydroxypyrrolidine and the dimethylacetal of 3,4-dihydroxypyrrolidine.

In yet a further aspect of the inventions $R^3$ is selected from hydroxypropyl, 2-butanol, 3-hydroxy-2-hydroxymethylpropyl, 2,3-dihydroxypropyl, 1,3-dihydroxyprop-2-yl, (2,2-dimethyl-1,3-dioxolan-4-yl)methyl, (2,2-dimethyl-1,3-dioxan-4-yl)methyl, (2,2-dimethyl-1,3-dioxan-5-yl)methyl, (2-oxo-1,3-dioxan-5-yl)methyl, cyanomethyl, butanoyl, methoxyethyl, (3-hydroxypiperidino)carbonylmethyl, 1,2,4-oxadiazolylmethyl, (5-oxo)-1,2,4-oxadiazolylmethyl, (5-methyl)-1,2,4-oxadiazolylmethyl, (2-amino)-1,3,4-oxadiazolylmethyl, tetrazolylmethyl, (3,4-dihydroxypyrrolidinyl)carbonylmethyl, [(3,4-dihydroxypyrrolidinyl)carbonylmethyl]dimethylacetal, methylthioethyl, methanesulfinylethyl, methanesulfonylethyl, N-methanesulfonamidocarbonylmethyl, N-methanesulfonamidocarbonylethyl, N-(1,3-dihydroxyprop-2-yl)carbamoylmethyl, 2-(dimethylamino)ethyl, 2-hydroxy-3-(dimethylamino)propyl, amino(N-hydroxy)iminomethyl, methoxycarbonylmethyl, hydroxymethylcarbonylmethyl, carboxymethyl, carbamoylmethyl, (dimethylcarbamoyl)methyl, (methylcarbamoyl)methyl, (methylcarbamoyl)ethyl, (hydroxycarbamoyl)methyl, (hydroxyethylcarbamoyl)methyl, and (methoxyethylcarbamoyl)methyl, acetylaminoethyl, trifluoroacetylaminoethyl, N-(pyrid-4-yl)carbamoylmethyl, N-(pyrid-2-yl)carbamoylmethyl, N-(3-methyl-pyrid-2-yl)carbamoylmethyl, N-(6-methyl-pyrid-2-yl)carbamoylmethyl, N-(3-hydroxy-pyrid-2-yl)carbamoylmethyl, N-(6-fluoro-pyrid-2-yl)carbamoylmethyl, N-(6-bromo-pyrid-2-yl)carbamoylmethyl, N-(6-fluoro-pyrid-3-yl)carbamoylmethyl, N-(6-chloro-pyrid-3-yl)carbamoylmethyl, N-(N-methyl-imidazol-3-yl)carbamoylmethyl, N-(imidazol-2-ylmethyl)carbamoylmethyl, N-(tetrazol-5-ylmethyl)carbamoylmethyl, N-(4-methyl-thiazol-2-yl)carbamoylmethyl, N-(1,3,4-thiadiazol-2-yl)carbamoylmethyl, N-(5-methyl-1,3,4-thiadiazol-2-yl)carbamoylmethyl, N-(5-ethyl-1,3,4-thiadiazol-2-yl)carbamoylmethyl, N-(4-cyano-pyridazin-3-yl)carbamoylmethyl, N-(6-chloro-pyridazin-3-yl)carbamoylmethyl, N-(2,4-dimethyl-2H-pyridazin-3-yl)carbamoylmethyl, N-(2-ethyl-2H-pyridazin-3-yl)carbamoylmethyl, N-(pyrazin-2-ylmethyl)carbamoylmethyl, N-(pyrimidin-4-yl)carbamoylmethyl, N-(2-hydroxy-pyrimidin-4-yl)carbamoylmethyl, N-(4-hydroxy-pyrimidin-2-yl)carbamoylmethyl, N-(N-methylpyrazol-3-yl)carbamoylmethyl, N-(5-ethylpyrazol-3-yl)carbamoylmethyl and N-(5-oxo-2H-pyrazol-3-yl)carbamoylmethyl.

In yet a further aspect of the inventions $R^3$ is selected from hydrogen, hydroxyethyl, 1,3-dihydroxyprop-2-yl, 2,3-dihydroxypropyl, 2,2-dimethyl-1,3-dioxan-5-ylmethyl, methylthioethyl, methanesulfinylethyl, methanesulfonylethyl, N-methanesulfonamidocarbonylethyl, amino(N-hydroxy)iminomethyl, methoxycarbonylmethyl, carboxymethyl, acetylaminoethyl, trifluoroacetylaminoethyl, hydroxymethylcarbonylmethyl, N-(pyrid-4-yl)carbamoylmethyl, N-(pyrid-2-yl)carbamoylmethyl, N-(3-methyl-pyrid-2-yl)carbamoylmethyl, N-(6-methyl-pyrid-2-yl)carbamoylmethyl, N-(3-hydroxy-pyrid-2-yl)carbamoylmethyl, N-(6-fluoro-pyrid-2-yl)carbamoylmethyl, N-(6-bromo-pyrid-2-yl)carbamoylmethyl, N-(6-fluoro-pyrid-3-yl)carbamoylmethyl, N-(6-chloro-pyrid-3-yl)carbamoylmethyl, N-(N-methyl-imidazol-3-yl)carbamoylmethyl, N-(imidazol-2-ylmethyl)carbamoylmethyl, N-(tetrazol-5-ylmethyl)carbamoylmethyl, N-(4-methyl-thiazol-2-yl)carbamoylmethyl, N-(1,3,4-thiadiazol-2-yl)carbamoylmethyl, N-(5-methyl-1,3,4-thiadiazol-2-yl)carbamoylmethyl, N-(5-ethyl-1,3,4-thiadiazol-2-yl)carbamoylmethyl, N-(4-cyano-pyridazin-3-yl)carbamoylmethyl, N-(6-chloro-pyridazin-3-yl)carbamoylmethyl, N-(2,4-dimethyl-2H-pyridazin-3-yl)carbamoylmethyl, N-(2-ethyl-2H-pyridazin-3-yl)

carbamoylmethyl, N-(pyrazin-2-ylmethyl)carbamoylmethyl, N-(pyrimidin-4-yl)carbamoylmethyl, N-(2-hydroxy-pyrimidin-4-yl)carbamoylmethyl, N-(4-hydroxy-pyrimidin-2-yl)carbamoylmethyl, N-(N-methylpyrazol-3-yl)carbamoylmethyl, N-(5-ethylpyrazol-3-yl)carbamoylmethyl and N-(5-oxo-2H-pyrazol-3-yl)carbamoylmethyl.

In yet a further aspect of the invention $R^3$ is selected from hydrogen, hydroxyethyl, hydroxypropyl, 2-butanol, 3-hydroxy-2-hydroxymethyl-propyl, 2,3-dihydroxypropyl, carbamoylmethyl, (dimethylcarbamoyl)methyl, (methylcarbamoyl)methyl, (methylcarbamoyl)ethyl, (hydroxycarbamoyl)methyl, (hydroxyethylcarbamoyl)methyl, (methoxyethylcarbamoyl)methyl, amino(N-hydroxy)iminomethyl, methanesulfinylethyl, and methanesulfonylethyl.

In one aspect, one of $R^9$ and $R^{10}$ is hydrogen and the other is selected from heterocyclyl and heterocyclyl($C_{1-4}$alkyl). Conveniently $R^9$ or $R^{10}$ as heterocyclyl and heterocyclyl ($C_{1-4}$ alkyl) is selected from oxazolyl, 1,3,4-oxadiazolyl, 1,2,4-oxadiazolyl, tetrazolyl, thiazoyl, thiadiazolyl, pyridyl, imidazolyl, furyl, thienyl, morpholine, pyrimidyl, pyrazinyl, pyridazinyl, pyrazolyl, pyrazolinyl, piperazinyl. morpholinomethyl, morpholinethyl, morpholinylmethyl, morpholinylethyl, piperidinomethyl, piperidinoethyl, piperidylmethyl, piperidylethyl, tetrahydrothiopyranyl, 1-oxotetrahydrothiopyranyl, 1,1-dioxotetrahydrothiopyranyl, imidazolylmethyl, imidazolylethyl, oxazolylmethyl, oxazolylethyl, 1,3,4-oxadiazolylmethyl, 1,2,4-oxadiazolylmethyl, 1,2,4-oxadiazolylethyl, pyridylmethyl, pyridylethyl, furylmethyl, furylethyl, (thienyl)methyl, (thienyl)ethyl, pyrazinylmethyl, pyrazinylethyl, piperazinylmethyl and piperazinylethyl; wherein the heterocylic ring is optional substituted on any available atom by 1, 2 or 3 substituents independently selected from halo, cyano, hydroxy, $C_{1-4}$alkyl, $C_{1-4}$alkoxy and $C_{1-4}$alkylS(O)$_b$ (wherein b is 0, 1 or 2), and additionally when the heterocyclyl ring is a heteroaryl ring, further suitable optional substituents are selected from nitro, amino, N-($C_{1-4}$alkyl)amino and N,N-($C_{1-4}$alkyl)$_2$amino, and/or wherein any heterocyclic ring is optionally oxidised such that a —$CH_2$— group is replaced by a —C(O)— and/or a ring sulphur atom is oxidised to form the S-oxide(s).

A preferred class of compound is of the formula (1) wherein;

----- is a single bond;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
$R^2$ is hydrogen;
$R^3$ is selected from cyano$C_{1-4}$alkyl, and $C_{1-4}$alkyl (optionally substituted by 1 or 2 $R^8$ groups);
$R^8$ is independently selected from hydroxy, $C_{3-7}$cycloalkyl, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, $C_{1-4}$alkoxy, $C_{1-4}$alkanoyl, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N($R^9$)($R^{10}$), —COOR$^9$, —C(O)NHSO$_2$Me, —C(=N—OH)NH$_2$, —C(=N—OH)NHC$_{1-4}$alkyl, —C(=N—OH)N($C_{1-4}$alkyl)$_2$, —C(=N—OH)NHC$_{3-6}$cycloalkyl, —C(=N—OH)N(C$_{3-6}$cycloalkyl)$_2$, —N(OH)CHO, —COCOOR$^9$, —NHC(O)R$^9$, ($R^9$)($R^{10}$)NSO$_2$—, —COCH$_2$OR$^{11}$ and —NHSO$_2$R$^9$;

$R^9$ and $R^{10}$ are independently selected from hydrogen, hydroxy, phenyl, heterocyclyl, heterocyclyl($C_{1-4}$alkyl), $C_{1-4}$alkyl (optionally substituted by 1 or 2 hydroxy groups) and $C_{1-4}$alkyl substituted by $C_{1-4}$alkoxy, and wherein $R^9$ and $R^{10}$ can together with the nitrogen to which they are attached form 4- to 6-membered ring where the ring is optionally substituted on carbon by 1 or 2 substituents selected from hydroxy or carboxy, or the ring may be optionally substituted on two adjacent carbons by O—$CH_2$—O— to form a cyclic acetal wherein one or both of the hydrogens of the —O—$CH_2$—O— group may be replaced by a methyl;

$R^{11}$ is selected from hydrogen, $C_{1-4}$alkyl and hydroxy$C_{1-4}$alkyl;
m is 1 or 2; and
$R^4$ is hydrogen or halo;

or a pharmaceutically acceptable salt or in vivo hydrolysable ester thereof.

Another preferred class of compounds is of formula (1) wherein:

----- is a single bond;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
$R^2$ is hydrogen;
$R^3$ is selected from $C_{1-4}$alkyl (optionally substituted by 1 or 2 $R^8$ groups);
$R^8$ is independently selected from hydroxy, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, $C_{1-4}$alkoxy, $C_{1-4}$alkanoyl, $C_{1-4}$alkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N($R^9$)($R^{10}$), —COOR$^9$, —C(O)NHSO$_2$Me, —C(=N—OH)NH$_2$, —C(=N—OH)NHC$_{1-4}$alkyl, —C(=N—OH)N($C_{1-4}$alkyl)$_2$ and —NHSO$_2$R$^9$;

$R^9$ and $R^{10}$ are independently selected from hydrogen, hydroxy, phenyl, heterocyclyl, heterocyclyl($C_{1-4}$alkyl), $C_{1-4}$alkyl (optionally substituted by 1 or 2 hydroxy groups) and $C_{1-4}$alkyl substituted by $C_{1-4}$alkoxy, and wherein $R^9$ and $R^{10}$ together with the nitrogen to which they are attached form a 4- to 6-membered ring selected from piperidine, 4-hydroxy piperidine, pyrrolidine, 3,4-dihydroxypyrrolidine and the dimethylacetal of 3,4-dihydroxypyrrolidine;
m is 1 or 2; and
$R^4$ is hydrogen or halo;

or a pharmaceutically acceptable salt or in vivo hydrolysable ester thereof.

Another preferred class of compound is of the formula (1) wherein:

----- is a single bond;
A is phenylene;
n is 0;
$R^2$ is hydrogen;
$R^3$ is selected from $C_{1-4}$alkyl (optionally substituted by 1 or 2 $R^8$ groups);
$R^8$ is independently selected from hydroxy, $C_{1-4}$alkylS(O)$_b$— (wherein b is 0, 1 or 2), —NHC(O)$R^9$ and —C(O)N($R^9$)($R^{10}$);
$R^9$ and $R^{10}$ are independently selected from hydrogen, $C_{1-4}$alkyl, heterocyclyl and heterocyclyl($C_{1-4}$alkyl);
m is 1 or 2; and
$R^4$ is halo;
or a pharmaceutically acceptable salt or in vivo hydrolysable ester thereof.

A further preferred class of compound is of the formula (1) wherein;

----- is a single bond;
A is phenylene;
n is 0, 1 or 2;
$R^1$ is independently selected from halo, cyano, nitro, hydroxy, fluoromethyl, difluoromethyl, trifluoromethyl, methoxy and, (when n is 2) methylenedioxy;
$R^2$ is hydrogen;
$R^3$ is selected from $C_{1-4}$alkyl (optionally substituted by 1 or 2 hydroxy groups provided that when there are 2 hydroxy groups they are not substituents on the same carbon);
m is 1 or 2;
$R^4$ is halo;
or a pharmaceutically acceptable salt or in vivo hydrolysable ester thereof.

A further preferred class of compound is of the formula (1) wherein;

----- is a single bond;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
$R^2$ is hydrogen;
$R^3$ is selected from groups of the formulae B and B':

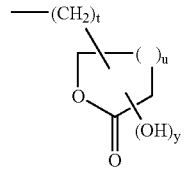

(B)

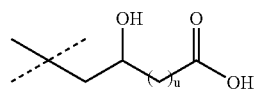

(B')

wherein y is 0 or 1, t is 0, 1, 2 or 3 and u is 1 or 2; provided that the hydroxy group is not a substituent on the ring carbon adjacent to the ring oxygen;
m is 1 or 2; and
$R^4$ is hydrogen or halo;
or a pharmaceutically acceptable salt or in vivo hydrolysable ester thereof.

A further preferred class of compound is of the formula (1) wherein;

----- is a single bond;
A is phenylene;
n is 0
$R^2$ is hydrogen;
$R^3$ is hydroxypropyl, dihydroxypropyl or dihydroxybutyl;
m is 1 or 2;
$R^4$ is hydrogen or halo;
or a pharmaceutically acceptable salt or in vivo hydrolysable ester thereof.

A further preferred class of compound is of the formula (1) wherein;

----- is a single bond;
A is phenylene;
n is 0;
$R^2$ is hydrogen;
$R^3$ is hydroxypropyl, dihydroxypropyl or dihydroxybutyl;
m is 1;
$R^4$ is chloro;
or a pharmaceutically acceptable salt or in vivo hydrolysable ester thereof.

A further preferred class of compound is of the formula (1) wherein;

----- is a single bond;
A is phenylene;
n is 0

R² is hydrogen;
R³ is heterocyclylcarbamoylmethyl;
m is 1 or 2;
R⁴ is hydrogen or halo;
or a pharmaceutically acceptable salt or in vivo hydrolysable ester thereof.

Another class of compounds is of the formula (1) wherein

----- is a double bond;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO₂Me and, (when n is 2) methylenedioxy;
$R^2$ is carboxy;
$R^3$ is selected from cyanoC$_{1-4}$alkyl, and C$_{1-4}$alkyl (optionally substituted by 1 or 2 $R^8$ groups);
$R^8$ is independently selected from hydroxy, C$_{3-7}$cycloalkyl, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, C$_{1-4}$alkoxy, C$_{1-4}$alkanoyl, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N(R⁹)(R¹⁰), —COOR⁹, —C(O)NHSO₂Me, —C(=N—OH)NH₂, —C(=N—OH)NHC$_{1-4}$alkyl, —C(=N—OH)N(C$_{1-4}$alkyl)₂—N(OH)CHO, —COCOOR⁹, —NHC(O)R⁹, (R⁹)(R¹⁰)NSO₂—, —COCH²OR¹¹ and —NHSO₂R⁹;

R⁹ and R¹⁰ are independently selected from hydrogen, hydroxy, phenyl, heterocyclyl, heterocyclyl(C$_{1-4}$alkyl), C$_{1-4}$alkyl (optionally substituted by 1 or 2 hydroxy groups) and C$_{1-4}$alkyl substituted by C$_{1-4}$alkoxy and wherein R⁹ and R¹⁰ can together with the nitrogen to which they are attached form 4- to 6-membered ring where the ring is optionally substituted on carbon by 1 or 2 substituents selected from hydroxy or carboxy, or the ring may be optionally substituted on two adjacent carbons by —O—CH₂—O— to form a cyclic acetal wherein one or both of the hydrogens of the —O—CH₂—O— group may be replaced by a methyl;
$R^{11}$ is selected from hydrogen, C$_{1-4}$alkyl and hydroxyC$_{1-4}$alkyl;
m is 1 or 2; and
R⁴ is hydrogen or halo;
or a pharmaceutically acceptable salt or in vivo hydrolysable ester thereof A further class of compound is of formula (1) wherein:

----- is a single bond;
A is heteroarylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO₂Me and, (when n is 2) methylenedioxy;
$R^2$ is hydrogen;
$R^3$ is selected from cyanoC$_{1-4}$alkyl, and C$_{1-4}$alkyl (optionally substituted by 1 or 2 $R^8$ groups)
$R^8$ is independently selected from hydroxy, C$_{3-7}$cycloalkyl, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, C$_{1-4}$alkoxy, C$_{1-4}$alkanoyl, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N(R⁹)(R¹⁰), —COOR⁹, —C(O)NHSO₂Me, —C(=N—OH)NH₂, —C(=N—OH) NHC$_{1-4}$alkyl, —C(=N—OH)N(C$_{1-4}$alkyl)₂, —N(OH)CHO, —COCOOR⁹, —NHC(O)R⁹, (R⁹)(R¹⁰)NSO₂—, —COCH²OR¹¹ and —NHSO₂R⁹;
R⁹ and R¹⁰ are independently selected from hydrogen, hydroxy, phenyl, heterocyclyl, heterocyclyl(C$_{1-4}$alkyl), C$_{1-4}$alkyl (optionally substituted by 1 or 2 hydroxy groups) and C$_{1-4}$alkyl substituted by C$_{1-4}$alkoxy and wherein R⁹ and R¹⁰ can together with the nitrogen to which they are attached form 4- to 6-membered ring where the ring is optionally substituted on carbon by 1 or 2 substituents selected from hydroxy or carboxy, or the ring may be optionally substituted on two adjacent carbons by —O—CH₂—O— to form a cyclic acetal wherein one or both of the hydrogens of the —O—CH₂—O— group may be replaced by a methyl;
$R^{11}$ is selected from hydrogen, C$_{1-4}$alkyl, hydroxyC$_{1-4}$alkyl;
m is 1 or 2;
R⁴ is hydrogen or halo;
or a pharmaceutically acceptable salt or in vivo hydrolysable ester thereof.

A further class of compound is of formula (1) wherein:

----- is a single bond;
A is heteroarylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO₂Me and, (when n is 2) methylenedioxy;
$R^2$ is hydrogen;
$R^3$ is selected from cyanoC$_{1-4}$alkyl, and C$_{1-4}$alkyl (optionally substituted by 1 or 2 $R^8$ groups)
$R^8$ is independently selected from hydroxy, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, C$_{1-4}$alkoxy, C$_{1-4}$alkanoyl, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N(R⁹)(R¹⁰), —COOR⁹, —C(O)NHSO₂Me, —C(=N—OH)NH$_{22}$, —C(=N—OH)NHC$_{1-4}$alkyl, —C(=N—OH)N(C$_{1-4}$alkyl)₂ and —NHSO₂R⁹;

$R^9$ and $R^{10}$ are independently selected from hydrogen, hydroxy, phenyl, heterocyclyl, heterocyclyl($C_{1-4}$alkyl), $C_{1-4}$alkyl (optionally substituted by 1 or 2 hydroxy groups) and $C_{1-4}$alkyl substituted by $C_{1-4}$alkoxy and wherein $R^9$ and $R^{10}$ can together with the nitrogen to which they are attached form 4- to 6-membered ring where the ring is optionally substituted on carbon by 1 or 2 substituents selected from hydroxy or carboxy or the ring may be optionally substituted on two adjacent carbons by —O—CH$_2$—O— to form a cyclic acetal wherein one or both of the hydrogens of the —O—CH$_2$—O— group may be replaced by a methyl;

m is 1 or 2; and $R^4$ is hydrogen or halo;

or a pharmaceutically acceptable salt or in vivo hydrolysable ester thereof.

A further class of compound is of formula (1) wherein:

----- is a single bond;
A is heteroarylene;
n is 0, 1 or 2;
$R^1$ is independently selected from halo, cyano, nitro, hydroxy, fluoromethyl, difluoromethyl, trifluoromethyl, methoxy and, (when n is 2) methylenedioxy;
$R^2$ is hydrogen;
$R^3$ is selected from cyano$C_{1-4}$alkyl, and $C_{1-4}$alkyl [optionally substituted by 1 or 2 $R^8$ groups];
wherein $R^8$ is independently selected from —C(O)N($R^9$)($R^{10}$), and —COO$R^9$, $R^9$ and $R^{10}$ are independently selected from hydrogen, $C_{1-4}$alkyl, heterocyclyl and heterocyclyl ($C_{1-4}$alkyl);
m is 1 or 2; and
$R^4$ is halo;
or a pharmaceutically acceptable salt or in vivo hydrolysable ester thereof.

A further class of compound is of formula (1) wherein:

----- is a single bond;
A is heteroarylene;
n is 0, 1 or 2;
$R^1$ is independently selected from halo, cyano, nitro, hydroxy, fluoromethyl, difluoromethyl, trifluoromethyl, methoxy and, (when n is 2) methylenedioxy;
$R^2$ is hydrogen;
$R^3$ is selected from $C_{1-4}$alkyl (optionally substituted by 1 or 2 hydroxy groups);
m is 1 or 2;
$R^4$ is halo;
or a pharmaceutically acceptable salt or in vivo hydrolysable ester thereof.

A preferred class of compound is of the formula (1) wherein;

----- is a single bond;

A is phenylene;

n is 1 or 2;

$R^1$ is independently selected from hydrogen, halo, nitro, cyano, hydroxy, fluoromethyl, difluoromethyl, trifluoromethyl and $R^1$ is of the formula A' or A":

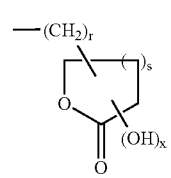

$$\text{—CH}_2\text{CH(OH)(CH}_2)_u\text{CO}_2\text{H} \qquad (A'')$$

wherein x is 0 or 1, r is 0, 1, 2 or 3 and s is 1 or 2; provided that the hydroxy group is not a substituent on the ring carbon adjacent to the ring oxygen;

$R^2$ is hydrogen;

$R^3$ is selected from $C_{1-4}$alkyl (optionally substituted by 1 or 2 hydroxy groups provided that when there are 2 hydroxy groups they are not substituents on the same carbon), cyano$C_{1-4}$alkyl, and $C_{1-4}$alkyl [substituted by 1 or 2 $R^8$ groups (provided that when there are 2 $R^8$ groups they are not substituents on the same carbon)];

{$R^8$ is independently selected from hydroxy, heterocyclyl, $C_{1-4}$alkanoyl, $C_{1-4}$alkoxy, $C_{1-4}$alkanesulfinyl, $C_{1-4}$alkanesulfonyl, —COCOO$R^9$, ($R^9$)($R^{10}$)NCO—, —COCH$_2$O$R^{11}$, ($R^9$)($R^{10}$)N—, —COO$R^9$ and 2,2-dimethyl-1,3-dioxolan-4-yl;

[$R^9$ and $R^{10}$ are independently selected from hydrogen, hydroxy, $C_{1-4}$alkyl (optionally substituted by 1 or 2 hydroxy groups provided that when there are 2 hydroxy groups they are not substituents on the same carbon) and $C_{1-4}$alkyl substituted by $C_{1-4}$alkoxy and wherein $R^9$ and $R^{10}$ can together with the nitrogen to which they are attached form 4- to 6-membered ring where the ring is optionally substituted on carbon by 1 or 2 substituents selected from hydroxy or carboxy;

$R^{11}$ is selected from hydrogen, $C_{1-4}$alkyl, $C_{1-4}$alkoxy and hydroxy$C_{1-4}$alkyl]};

m is 1 or 2;

$R^4$ is hydrogen or halo.

A further preferred class of compound is of the formula (1) wherein;

----- is a single bond;

A is phenylene;

n is 1 or 2;

$R^1$ is independently selected from hydrogen, halo, nitro, hydroxy, $C_{1-4}$alkyl and $R^1$ is of the formula A' or A":

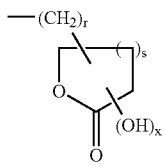 (A')

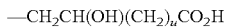 (A")

wherein x is 0 or 1, r is 0, 1, 2 or 3 and s is 1 or 2; provided that the hydroxy group is not a substituent on the ring carbon adjacent to the ring oxygen;

$R^2$ is hydrogen;

$R^3$ is selected from $C_{1-4}$alkyl (optionally substituted by 1 or 2 hydroxy groups provided that when there are 2 hydroxy groups they are not substituents on the same carbon);

m is 1 or 2;

$R^4$ is hydrogen or halo.

In another aspect of the invention, preferred compounds of the invention are any one of:

5-chloro-N-[1-(methoxycarbonylmethyl)-2-oxo-1,2,3,4-tetrahydroquinolin-3-yl]-1H-indole-2-carboxamide;

N-[1-(carboxymethyl)-2-oxo-1,2,3,4-tetrahydroquinolin-3-yl]-5-chloroindole-2-carboxamide;

5-chloro-N-(2-oxo-1,2,3,4-tetrahydroquinolin-3-yl)-1H-indole-2-carboxamide;

5-chloro-N-[{2-oxo-1-[2-oxo-2-(pyridin-2-ylamino)ethyl]-1,2,3,4-tetrahydroquinolin-3-yl}-1H-indole-2-carboxamide;

5-chloro-N-{1-[2-(methylthio)ethyl]-2-oxo-1,2,3,4-tetrahydroquinolin-3-yl}-1H-indole-2-carboxamide;

5-chloro-N-{1-[2-(methylsulphinyl)ethyl]-2-oxo-1,2,3,4-tetrahydroquinolin-3-yl}-1H-indole-2-carboxamide;

5-chloro-N-{1-[2-(methylsulphonyl)ethyl]-2-oxo-1,2,3,4-tetrahydroquinolin-3-yl}-1H-indole-2-carboxamide;

5-chloro-N-{2-oxo-1-[2-oxo-2-(1,3,4-thiadiazol-2-ylamino)ethyl]-1,2,3,4-tetrahydroquinolin-3-yl}1H-indole-2-carboxamide;

5-chloro-N-(1-{2-[(6-methylpyridin-2-yl)amino]-2-oxoethyl}-2-oxo-1,2,3,4-tetrahydroquinolin-3-yl)-1H-indole-2-carboxamide;

5-chloro-N-{2-oxo-1-[2-oxo-2-(pyridin-3-ylamino)ethyl]-1,2,3,4-tetrahydroquinolin-3-yl}-1H-indole-2-carboxamide;

5-chloro-N-(1-{2-[(5-methyl-1,3,4-thiadiazol-2-yl)amino]-2-oxoethyl}-2-oxo-1,2,3,4-tetrahydroquinolin-3-yl)-1H-indole-2-carboxamide;

5-chloro-N-(1-{2-[(5-ethyl-1,3,4-thiadiazol-2-yl)amino]-2-oxoethyl}-2-oxo-1,2,3,4-tetrahydroquinolin-3-yl)-1H-indole-2-carboxamide;

5-chloro-N-(1-{2-[(4-cyano-1H-pyrazol-3-yl)amino]-2-oxoethyl}-2-oxo-1,2,3,4-tetrahydroquinolin-3-yl)-1H-indole-2-carboxamide;

5-chloro-N-(1-{2-[(4-methyl-1,3-thiazol-2-yl)amino]-2-oxoethyl}-2-oxo-1,2,3,4-tetrahydroquinolin-3-yl)-1H-indole-2-carboxamide;

5-chloro-N-(1-{2-[(6-chloropyridin-3-yl)amino]-2-oxoethyl}-2-oxo-1,2,3,4-tetrahydroquinolin-3-yl)-1H-indole-2-carboxamide;

5-chloro-N-(1-{2-[(3-hydroxypyridin-2-yl)amino]-2-oxoethyl}-2-oxo-1,2,3,4-tetrahydroquinolin-3-yl)-1H-indole-2-carboxamide;

5-chloro-N-(2-oxo-1-{2-oxo-2-[(pyridin-2-ylmethyl)amino]ethyl}-1,2,3,4-tetrahydroquinolin-3-yl)-1H-indole-2-carboxamide;

5-chloro-N-{2-oxo-1-[2-oxo-2-(pyridin-4-ylamino)ethyl]-1,2,3,4-tetrahydroquinolin-3-yl}-1H-indole-2-carboxamide;

5-chloro-N-(1-{2-[(1-methyl-1H-pyrazol-5-yl)amino]-2-oxoethyl}-2-oxo-1,2,3,4-tetrahydroquinolin-3-yl)-1H-indole-2-carboxamide;

5-chloro-N-(1-{2-[(1,3-dimethyl-1H-pyrazol-5-yl)amino]-2-oxoethyl}-2-oxo-1,2,3,4-tetrahydroquinolin-3-yl)-1H-indole-2-carboxamide;

5-chloro-N-(2-oxo-1-{2-oxo-2-[(pyrazin-2-ylmethyl)amino]ethyl}-1,2,3,4-tetrahydroquinolin-3-yl)-1H-indole-2-carboxamide;

5-chloro-N-(1-{2-[(6-fluoropyridin-3-yl)amino]-2-oxoethyl}-2-oxo-1,2,3,4-tetrahydroquinolin-3-yl)-1H-indole-2-carboxamide;

5-chloro-N-(1-{2-[(2-hydroxypyrimidin-4-yl)amino]-2-oxoethyl}-2-oxo-1,2,3,4-tetrahydroquinolin-3-yl)-1H-indole-2-carboxamide;

5-chloro-N-{2-oxo-1-[2-oxo-2-(pyrimidin-4-ylamino)ethyl]-1,2,3,4-tetrahydroquinolin-3-yl}-1H-indole-2-carboxamide;

5-chloro-N-(1-{2-[(1-ethyl-1H-pyrazol-5-yl)amino]-2-oxoethyl}-2-oxo-1,2,3,4-tetrahydroquinolin-3-yl)-1H-indole-2-carboxamide;

5-chloro-N-(2-oxo-1-{2-oxo-2-[(5-oxo-4,5-dihydro-1H-pyrazol-3-yl)amino]ethyl{-1,2,3,4-tetrahydroquinolin-3-yl)-1H-indole-2-carboxamide;

5-chloro-N-(1-{2-[(4-hydroxypyrimidin-2-yl)amino]-2-oxoethyl}-2-oxo-1,2,3,4-tetrahydroquinolin-3-yl)-1H-indole-2-carboxamide;

5-chloro-N-(1-{2-[(3-methylpyridin-2-yl)amino]-2-oxoethyl}-2-oxo-1,2,3,4-tetrahydroquinolin-3-yl)-1H-indole-2-carboxamide;

5-chloro-N-(1-{2-[(6-chloropyridazin-3-yl)amino]-2-oxoethyl}-2-oxo-1,2,3,4-tetrahydroquinolin-3-yl)-1H-indole-2-carboxamide;

5-chloro-N-(1-{2-[(1H-imidazol-2-ylmethyl)amino]-2-oxoethyl}-2-oxo-1,2,3,4-tetrahydroquinolin-3-yl)-1H-indole-2-carboxamide;

5-chloro-N-(1-{2-[(1-methyl-1H-pyrazol-3-yl)amino]-2-oxoethyl}-2-oxo-1,2,3,4-tetrahydroquinolin-3-yl)-1H-indole-2-carboxamide;

5-chloro-N-{2-oxo-1-[2-oxo-2-(2H-tetrazol-5-ylamino)ethyl]-1,2,3,4-tetrahydroquinolin-3-yl}-1H-indole-2-carboxamide;

5-chloro-N-(1-{2-[(3-ethyl-1H-pyrazol-5-yl)amino]-2-oxoethyl}-2-oxo-1,2,3,4-tetrahydroquinolin-3-yl)-1H-indole-2-carboxamide;

5-chloro-N-(1-{2-[(5-fluoropyridin-2-yl)amino]-2-oxoethyl}-2-oxo-1,2,3,4-tetrahydroquinolin-3-yl)-1H-indole-2-carboxamide;

N-(1-{2-[(6-bromopyridin-3-yl)amino]-2-oxoethyl}-2-oxo-1,2,3,4-tetrahydroquinolin-3-yl)-5-chloro-1H-indole-2-carboxamide;

5-chloro-N-[1-(2-hydroxyethyl)-2-oxo-1,2,3,4-tetrahydroquinolin-3-yl]-1H-indole-2-carboxamide;

5-chloro-N-{1-[(2,2-dimethyl-1,3-dioxan-5-yl)methyl]-2-oxo-1,2,3,4-tetrahydroquinolin-3-yl}-1H-indole-2-carboxamide;

5-chloro-N-{1-[3-hydroxy-2-(hydroxymethyl)propyl]-2-oxo-1,2,3,4-tetrahydroquinolin-3-yl}-1H-indole-2-carboxamide;

5-chloro-N-[1-(2,3-dihydroxypropyl)-2-oxo-1,2,3,4-tetrahydroquinolin-3-yl]-1H-indole-2-carboxamide;

5-chloro-N-[1-(3-hydroxy-2-oxopropyl)-2-oxo-1,2,3,4-tetrahydroquinolin-3-yl]-1H-indole-2-carboxamide;

5-chloro-N-{1-[(2R)-2,3-dihydroxypropyl]-2-oxo-1,2,3,4-tetrahydroquinolin-3-yl}-1H-indole-2-carboxamide;

5-chloro-N-(1-{2-[(methylsulfonyl)amino]ethyl}-2-oxo-1,2,3,4-tetrahydroquinolin-3-yl)-1H-indole-2-carboxamide;

N-{1-[2-(acetylamino)ethyl]-2-oxo-1,2,3,4-tetrahydroquinolin-3-yl}-5-chloro-1H-indole-2-carboxamide;

5-chloro-N-(2-oxo-1-{2-[(trifluoroacetyl)amino]ethyl}-1,2,3,4-tetrahydroquinolin-3-yl)-1H-indole-2-carboxamide;

5-chloro-N-[1-(3-hydroxypropyl)-2-oxo-1,2,3,4-tetrahydroquinolin-3-yl]-1H-indole-2-carboxamide;

N-{1-[(2Z)-2-amino-2-(hydroxyimino)ethyl]-2-oxo-1,2,3,4-tetrahydroquinolin-3-yl}-5-chloro-1H-indole-2-carboxamide;

5-chloro-N-(6-fluoro-2-oxo-1,2,3,4-tetrahydroquinolin-3-yl)-1H-indole-2-carboxamide; and 5-chloro-N-[6-(methyloxy)-2-oxo-1,2,3,4-tetrahydroquinolin-3-yl]-1H-indole-2-carboxamide;

or a pharmaceutically acceptable salt or an in vivo hydrolysable ester thereof.

In another aspect of the invention, further preferred compounds of the invention are any one of:

5-chloro-N-[1-(2-hydroxyethyl)-2-oxo-1,2,3,4-tetrahydroquinolin-3-yl]-1H-indole-2-carboxamide;

5-chloro-N-{1-[3-hydroxy-2-(hydroxymethyl)propyl]-2-oxo-1,2,3,4-tetrahydroquinolin-3-yl}-1H-indole-2-carboxamide;

5-chloro-N-[1-(2,3-dihydroxypropyl)-2-oxo-1,2,3,4-tetrahydroquinolin-3-yl]-1H-indole-2-carboxamide; and 5-chloro-N-{1-[(2R)-2,3-dihydroxypropyl]-2-oxo-1,2,3,4-tetrahydroquinolin-3-yl}-1H-indole-2-carboxamide;

or a pharmaceutically acceptable salt or an in vivo hydrolysable ester thereof.

In another aspect of the invention, further preferred compounds of the invention are any one of:

5-chloro-N-[1-(2,3-dihydroxypropyl)-2-oxo-1,2,3,4-tetrahydroquinolin-3-yl]-1H-indole-2-carboxamide; and 5-chloro-N-{1-[(2R)-2,3-dihydroxypropyl]-2-oxo-1,2,3,4-tetrahydroquinolin-3-yl}-1H-indole-2-carboxamide;

or a pharmaceutically acceptable salt or an in vivo hydrolysable ester thereof.

Another aspect of the present invention provides a process for preparing a compound of formula (1) or a pharmaceutically acceptable salt or an in vivo hydrolysable ester thereof which process (wherein A, $R^1$, $R^2$, $R^3$, $R^4$, m, n and - - - are, unless otherwise specified, as defined in formula (1)) comprises of:

a) reacting an acid of the formula (2):

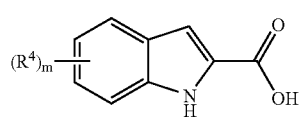

(2)

or an activated derivative thereof; with an amine of formula (3):

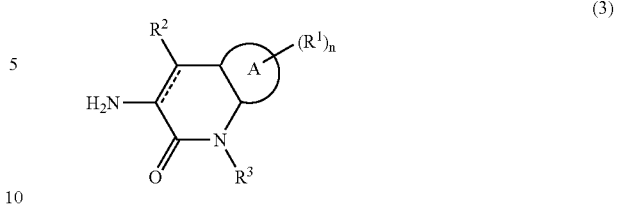

(3)

and thereafter if necessary:

i) converting a compound of the formula (1) into another compound of the formula (1);

ii) removing any protecting groups;

iii) forming a pharmaceutically acceptable salt or in vivo hydrolysable ester.

Specific reaction conditions for the above reaction are as follows.

Process a) Acids of formula (2) and amines of formula (3) may be coupled together in the presence of a suitable coupling reagent. Standard peptide coupling reagents known in the art can be employed as suitable coupling reagents, or for example carbonyldiimidazole, 1-ethyl-3-(3-dimethylaminopropyl)carbodi-imide hydrochloride (EDCI) and dicyclohexyl-carbodiimide (DCCI), optionally in the presence of a catalyst such as 1-hydroxybenzotriazole, dimethylaminopyridine or 4-pyrrolidinopyridine, optionally in the presence of a base for example triethylamine, di-isopropylethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Where $R^3$ of formula (1) contains an ester group, the conversion of a compound of the formula (1) into another compound of the formula (1) may involve hydrolysis of the ester group for example, acid or base hydrolysis, for example using lithium hydroxide. The reaction of this type is well known in the art.

Where $R^3$ of formula (1) contains —COOH group, the conversion of a compound of the formula (1) into another compound of the formula (1) may involve reduction of this group using reducing agents such as lithium borohydride, sodium borohydride etc. The conversion may also involve the coupling of this —COOH group with ammonia or a substituted amine in the presence of a base for example triethylamine, di-isopropylethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide.

Substituted amides wherein $R^3$ is $CH_2C(O)N(R^9)(R^{10})$ may be prepared from the corresponding acids by a coupling reaction using the appropriate amine in the presence of a coupling reagent, for example EDCI. Alternatively, the acid may first be converted to a mixed anhydride, by reaction with, for example, ethyl chloroformate, which is reacted with an appropriate amine to produce the substituted amide. Substituted sulphonamides wherein $R^3$ is $CH_2C(O)NHSO_2R_9$ may be prepared similarly, for instance by coupling the compounds wherein $R^3$ is $CH_2CO_2H$ with the appropriate substituted sulphonamide in the presence of a coupling reagent, for example EDCI.

Compounds of formula (1) wherein $R^3$ is 2-hydroxymethyl may be prepared by reduction of the mixed anhydrides described above with, for example, lithium borohydride. Compounds of formula (1) wherein $R^3$ is an oxadiazol-5-ylmethyl group may be prepared by reaction of the mixed anhydrides described above with an appropriately substituted hydroxyamidine, for example N'-hydroxyethanimidamide, in the presence of a base such as N-methylmorpholine.

Compounds of formula (1) wherein $R^3$ is a tetrazol-5-ylmethyl group may be prepared by reaction of the corresponding compounds where $R^3$ is a cyanomethyl group with an azide, for example sodium azide, in the presence of an amine salt, for instance triethylamine hydrochloride. Compounds of formula (1) wherein $R^3$ is 2-amino-2-(hydroxyimino)ethyl may be prepared by reaction of compounds wherein $R^3$ is cyanomethyl with hydroxylamine hydrochloride in the presence of a base, for example sodium methoxide.

Compounds of formula (1) wherein $R^3$ is a 2-(methylsulphonyl)ethyl or 2-(methylsulphinyl)ethyl group may be prepared by reaction of the corresponding compounds where $R^3$ is 2-methylthioethyl with an oxidising agent, for example oxone.

Compounds of formula (1) wherein $R^3$ is a dihydroxyalkyl group, for example 2,3-dihydroxypropyl or 2-(hydroxymethyl)-3-hydroxypropyl may be prepared by acid hydrolysis of the corresponding compounds of formula (1) wherein $R^3$ is a protected dihydroxyalkyl group for example (2,2-dimethyl-1,3-dioxan-5-yl)methyl, (2,2-dimethyl-1,3-dioxolan-4-yl)methyl or (2-oxo-1,3-dioxan-5-yl)methyl.

The acids of formula (2) are commercially available or they are know compounds or they are prepared by processes known in the art.

Compounds of formula (3) may be prepared by reacting an amine of formula (4)

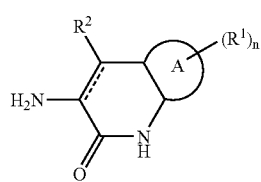

(4)

with $R^3$-L where L is a suitable leaving group (for example chloro, bromo or iodo) in the presence of a base such as sodium hydride in a suitable solvent.

Compounds of the formula (4) wherein A is phenylene and

----- is a single bond may be made from 3-amino-3,4-dihydroquinolin-2-(1H)-one hydrochloride (*J. Med. Chem.*, 28, 1985, 1511–16). Compounds of the formula (4) wherein A is phenylene and

----- is a double bond may be prepared by the reductive cyclisation of a compound of formula (5), using for example tin (II) chloride in hydrochloric acid, followed by removal of the Boc protecting group, using for example trifluoroacetic acid. Compounds of formula (5) may be prepared by reaction of compounds of formula (6) by reaction with a compound of formula (7) in the presence of a base, for example tetramethylguanidine. Compounds of formula (6) are commercially available or described in the literature.

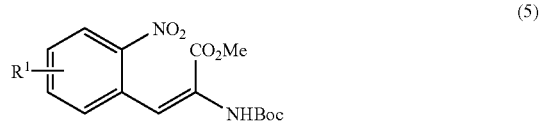

(5)

(6)

(7)

Compounds of the formula (4) wherein A is heterocyclylene can be prepared from cyclisation of suitably functionalised heterocycles. For example, when A is pyridine,

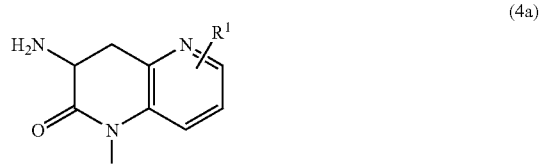

(4a)

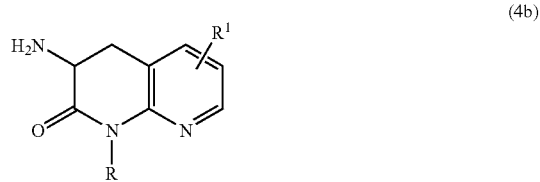

(4b)

compounds of formula (4a) and (4b) may be prepared from an appropriately substituted nitro-methylpyridine or aminopyridine according to the Schemes 2 and 3:—

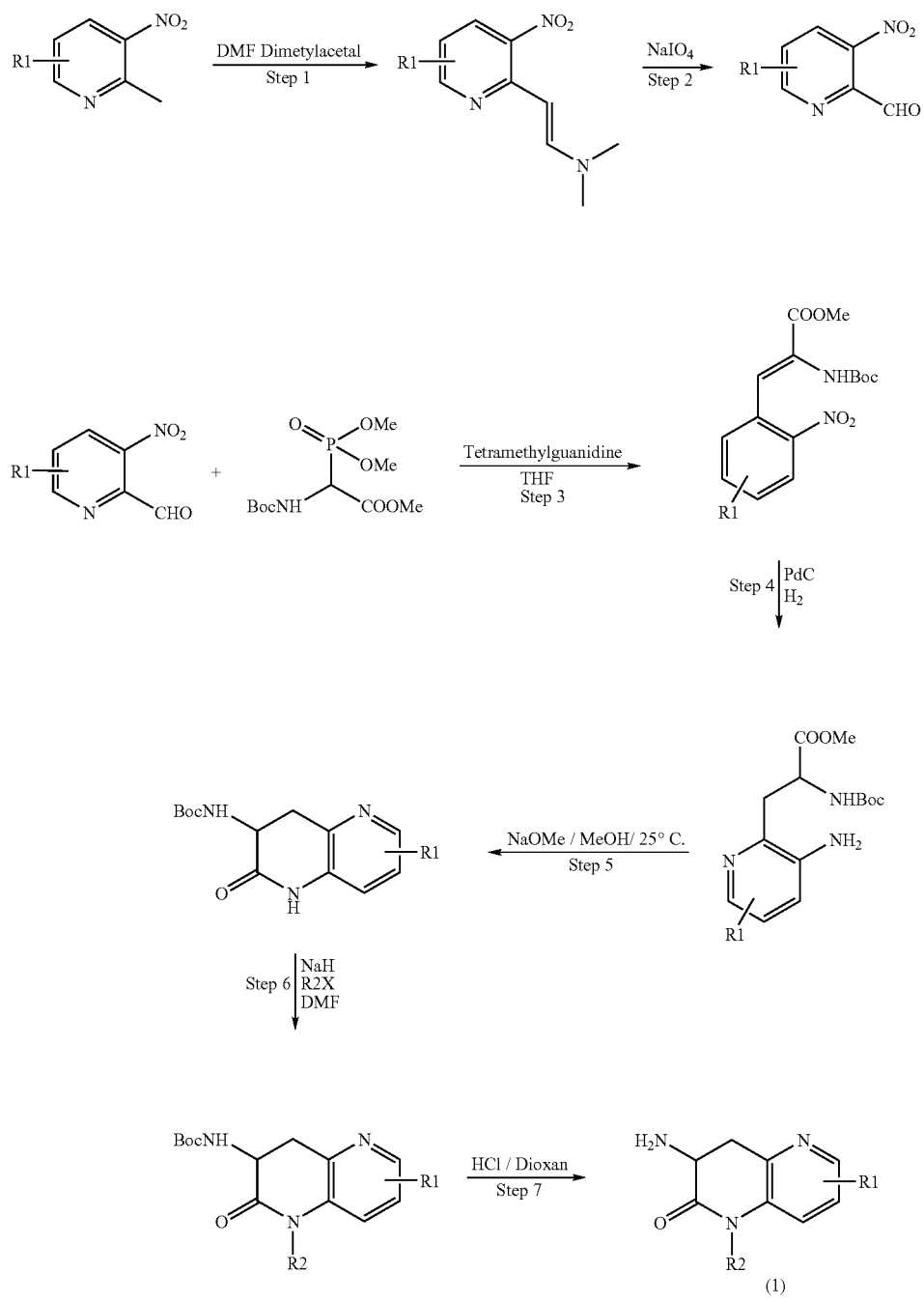

Steps 1 and 2 may be carried out by the process described in Tetrahedron 1998, 54(23), 6311–6318.

Step 3 may be carried out by the method described in Synthesis 1992 (5), 487. Assymetric hydrogenation reactions of olefins as shown in Step 4 are well known (see for example, JACS 1993, 115, 10125–10138) and lead to homochiral final products.

Step 5 may alternatively be carried out by hydrolysing the ester and activating the resulting acid with a carbodiimide such as EDCI or DCCI, or by preparing an acid chloride, or activated ester such as an N-hydroxysuccinimide ester. Suitable bases are organic base such as triethylamine or di-isopropylethylamine (DIPEA) or 1,8-diazabicyclo[5.4.0]undec-7-ene (DBU).

In Step 6 X is a leaving group, for example Cl, Br, I, OMesyl. In Step 7 alternative solvents such as dichloromethane or other acids such as trifluoroacetic acid can be used.

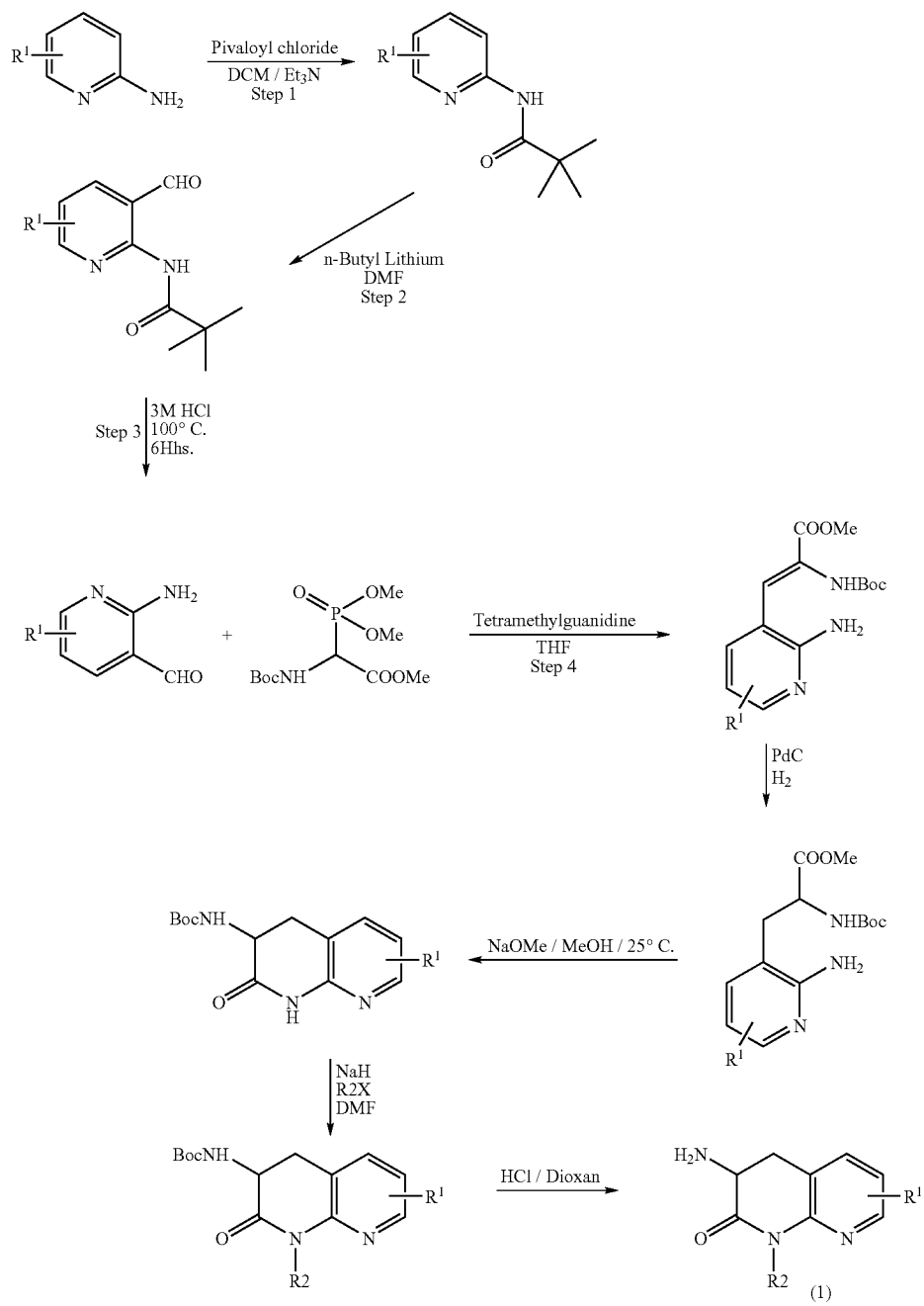

Steps 1, 2, 3 and 4 are Described in JOC 1983, 48, 3401–3408.

The processes described above and shown in Schemes 2 and 3 may also be applied to other isomeric pyridines or six membered heterocycles containing more than one nitrogen.

Compounds of the formula (4) wherein A is a heterocyclene and there is a bridgehead nitrogen, for example a compound of formula (4c), may be prepared by cyclisation of a compound of the formula (8):

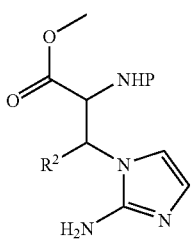

(8)

wherein P is an amino protecting group such as triphenylmethyl. This transformation is induced by heating compounds of the formula (8) to reflux in a solvent, for example, ethanol.

Compounds of the formula (8) may be prepared from a compound of the formula (9) by hydrogenation using a catalyst such as Pd/C at ambient temperature.

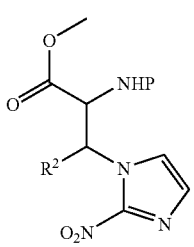

(9)

Compounds of the formula (9) may be prepared from compounds of the formula (10) and (11):

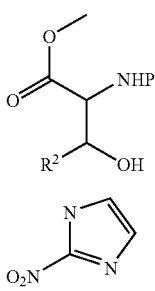

(10)

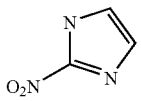

(11)

using conditions known for the Mitsunobu reaction (*Bull. Chem. Soc. Jpn.*, 1967, 40 2380). Compounds of the formulae (10) and (11) are commercially available.

Compounds of the formula (4) wherein A is heteroarylene and there is a bridgehead heteroatom, for example, compounds of the formula (4d) may be made by analogous chemistry to that shown for making compounds of the formula (4c).

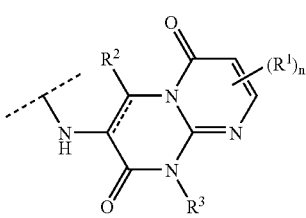

(4d)

It will be appreciated that certain of the various ring substituents in the compounds of the present invention, for example $R^1$ and $R^4$, may be introduced by standard aromatic substitution reactions or generated by conventional functional group modifications either prior to or immediately following the processes mentioned above, and as such are included in the process aspect of the invention. Such reactions may convert one compound of the formula (1) into another compound of the formula (1). Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkanesulphinyl or alkanesulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain intermediates in the preparation of a compound of the formula (1) are novel and form another aspect of the invention.

As stated hereinbefore the compounds defined in the present invention possesses glycogen phosphorylase inhibitory activity. This property may be assessed, for example, using the procedure set out below.

Assay

The activity of the compounds is determined by measuring the inhibitory effect of the compounds in the direction of glycogen synthesis, the conversion of glucose-1-phosphate into glycogen with the release of inorganic phosphate, as described in EP 0 846 464 A2. The reactions were in 96well microplate format in a volume of 100 μl. The change in optical density due to inorganic phosphate formation was measured at 620 nM in a Labsystems iEMS Reader MF by the general method of (Nordlie R. C and Arion W. J, Methods of Enzymology, 1966, 619–625). The reaction is in 50 mM HEPES (N-(2-Hydroxyethyl)piperazine-N'-(2-ethanesulfonic acid); 4-(2-Hydroxyethyl)piperazine-1-ethanesulfonic acid), 2.5 mM MgCl$_2$, 2.25 mM ethylene glycol-bis(b-aminoethyl ether) N,N,N'N'-tetraacetic acid, 100 mM KCl, 2 mM D-(+)-glucose pH7.2, containing 0.5 mM dithiothreitol, the assay buffer solution, with 0.1 mg type III glycogen, 0.15 ug glycogen phosphorylase a (GPa) from rabbit muscle and 0.5 mM glucose-1-phosphate. GPa is pre-incubated in the assay buffer solution with the type III glycogen at 2.5 mg ml$^{-1}$ for 30 minutes. 40 μl of the enzyme solution is added to 25 μl assay buffer solution and the reaction started with the addition of 25 μl 2 mM glucose-1-phosphate. Compounds to be tested are prepared in 10 μl 10% DMSO in assay buffer solution, with final concentration of 1% DMSO in the assay. The non-inhibited activity of GPa is measured in the presence of 10 μl 10% DMSO in assay buffer solution and maximum inhibition measured in the presence of 30 μM CP320626 (Hoover et al (1998) J Med Chem 41, 2934–8; Martin et al (1998) PNAS 95, 1776–81). The reaction is stopped after 30 min with the addition of 50 μl acidic ammonium molybdate solution, 12 ug ml$^{-1}$ in 3.48% H$_2$SO$_4$ with 1% sodium lauryl sulphate and 10 ug ml$^{-1}$ ascorbic acid. After 30 minutes at room temperature the absorbency at 620 nm is measured.

The assay is performed at a test concentration of inhibitor of 10 μM or 100 μM. Compounds demonstrating significant inhibition at one or both of these concentrations may be further evaluated using a range of test concentrations of inhibitor to determine an IC$_{50}$, a concentration predicted to inhibit the enzyme reaction by 50%.

Activity is calculated as follows:—

% inhibition=(1−(compound OD620−fully inhibited OD620)/(non-inhibited rate OD620−fully inhibited OD620))*100.

OD620=optical density at 620 nM.

Typical IC$_{50}$ values for compounds of the invention when tested in the above assay are in the range 100 μM to 1 nM.

The activity of the compounds is alternatively determined by measuring the inhibitory effect of the compounds on glycogen degradation, the production of glucose-1-phosphate from glycogen is monitored by the multienzyme coupled assay, as described in EP 0 846 464 A2, general method of Pesce et al (Pesce, M A, Bodourian, S H, Harris, R C, and Nicholson, J F (1977) Clinical Chemistry 23, 1171–1717). The reactions were in 384well microplate format in a volume of 50 μl. The change in fluorescence due to the conversion of the co-factor NAD to NADH is measured at 340 nM excitation, 465 nm emission in a Tecan Ultra Multifunctional Microplate Reader. The reaction is in 50 mM HEPES, 3.5 mM KH$_2$PO$_4$, 2.5 mM MgCl$_2$, 2.5 mM ethylene glycol-bis(b-aminoethyl ether) N,N,N'N'tetraacetic acid, 100 mM KCl, 8 mM D-(+)-glucose pH7.2, containing 0.5 mM dithiothreitol, the assay buffer solution. Human recombinant liver glycogen phosphorylase a (hrl GPa) 20 nM is pre-incubated in assay buffer solution with 6.25 mM NAD, 1.25 mg type III glycogen at 1.25 mg ml$^{-1}$ the reagent buffer, for 30 minutes. The coupling enzymes, phosphoglucomutase and glucose-6-phosphate dehydrogenase (Sigma) are prepared in reagent buffer, final concentration 0.25 Units per well. 20 μl of the hrl GPa solution is added to 10 μl compound solution and the reaction started with the addition of 20 ul coupling enzyme solution. Compounds to be tested are prepared in 10 μl 5% DMSO in assay buffer solution, with final concentration of 1% DMSO in the assay. The non-inhibited activity of GPa is measured in the presence of 10 μl 5% DMSO in assay buffer solution and maximum inhibition measured in the presence of 5 mgs ml$^{-1}$ N-ethylmaleimide. After 6 hours at 30° C. Relative Fluoresence Units (RFUs) are measured at 340 nM excitation, 465 nm emission.

The assay is performed at a test concentration of inhibitor of 10 μM or 100 μM. Compounds demonstrating significant inhibition at one or both of these concentrations may be further evaluated using a range of test concentrations of inhibitor to determine an IC$_{50}$, a concentration predicted to inhibit the enzyme reaction by 50%.

Activity is calculated as follows:—

% inhibition=(1−(compound RFUs−fully inhibited RFUs)/(non-inhibited rate RFUs−fully inhibited RFUs))*100.

Typical IC$_{50}$ values for compounds of the invention when tested in the above assay are in the range 100 μM to 1 nM. For example, Example 14 was found to have an IC$_{50}$ of 4.6 μm.

Rat hepatocytes were isolated by the collagenase perfusion technique, general method of Seglen (P. O. Seglen, Methods Cell Biology (1976) 13 29–83). Cells were cultured on Nunclon six well culture plates in DMEM (Dulbeco's Modified Eagle's Medium) with high level of glucose containing 10% foetal calf serum, NEAA (non essential amino acids), Glutamine, penicillin/streptomycin ((100 units/100 ug)/ml) for 4 to 6 hours. The hepatocytes were then cultured in the DMEM solution without foetal calf serum and with 10 nM insulin and 10 nM dexamethasone. Experiments were initiated after 18–20 hours culture by washing the cells and adding Krebs-Henseleit bicarbonate buffer containing 2.5 mM $CaCl_2$ and 1% gelatin. The test compound was added and 5 minutes later the cells were challenged with 25 nM glucagon. The Krebs-Henseleit solution was removed after 60 min incubation at 37° C., 95% $O_2$/5% $CO_2$ and the glucose concentration of the Krebs-Henseleit solution measured.

According to a further aspect of the invention there is provided a pharmaceutical composition which comprises a compound of the formula (1), or a pharmaceutically acceptable salt or in vivo hydrolysable ester thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The compound of formula (1) will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The inhibition of glycogen phosphorylase activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. Simultaneous treatment may be in a single tablet or in separate tablets. For example in the treatment of diabetes mellitus chemotherapy may include the following main categories of treatment:

1) Insulin and insulin analogues;
2) Insulin secretagogues including sulphonylureas (for example glibenclamide, glipizide) and prandial glucose regulators (for example repaglinide, nateglinide);
3) Insulin sensitising agents including PPARg agonists (for example pioglitazone and rosiglitazone);
4) Agents that suppress hepatic glucose output (for example metformin).
5) Agents designed to reduce the absorption of glucose from the intestine (for example acarbose);
6) Agents designed to treat the complications of prolonged hyperglycaemia;
7) Anti-obesity agents (for example sibutramine and orlistat);
8) Anti-dyslipidaemia agents such as, HMG-CoA reductase inhibitors (statins, eg pravastatin); PPARct agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
9) Antihypertensive agents such as, P blockers (eg atenolol, inderal); ACE inhibitors (eg lisinopril); Calcium antagonists (eg. nifedipine); Angiotensin receptor antagonists (eg candesartan), a antagonists and diuretic agents (eg. furosemide, benzthiazide);
10) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin; and
11) Anti-inflammatory agents, such as non-steroidal anti-inflammatory drugs (eg. aspirin) and steroidal anti-inflammatory agents (eg. cortisone).

According to a further aspect of the present invention there is provided a compound of the formula (1), or a pharmaceutically acceptable salt or in vivo hydrolysable ester thereof, as defined hereinbefore, for use in a method of treatment of a warm-blooded animal such as man by therapy.

According to an additional aspect of the invention there is provided a compound of the formula (1), or a pharmaceutically acceptable salt or in vivo hydrolysable ester thereof, as defined hereinbefore, for use as a medicament.

According to an additional aspect of the invention there is provided a compound of the formula (1), or a pharmaceutically acceptable salt or in vivo hydrolysable ester thereof, as defined hereinbefore, for use as a medicament in the treatment of type 2 diabetes, insulin resistance, syndrome X, hyperinsulinaemia, hyperglucagonaemia, cardiac ischaemia or obesity in a warm-blooded animal such as man.

According to this another aspect of the invention there is provided the use of a compound of the formula (1), or a pharmaceutically acceptable salt or in vivo hydrolysable ester thereof, as defined hereinbefore in the manufacture of a medicament for use in the treatment of type 2 diabetes, insulin resistance, syndrome X, hyperinsulinaemia, hyperglucagonaemia, cardiac ischaemia or obesity in a warm-blooded animal such as man.

According to this another aspect of the invention there is provided the use of a compound of the formula (1), or a pharmaceutically acceptable salt or in vivo hydrolysable ester thereof, as defined hereinbefore in the manufacture of a medicament for use in the treatment of type 2 diabetes in a warm-blooded animal such as man.

According to a further feature of this aspect of the invention there is provided a method of producing a glycogen phosphorylase inhibitory effect in a warm-blooded animal, such as man, in need of such treatment which comprises administering to said animal an effective amount of a compound of formula (1).

According to this further feature of this aspect of the invention there is provided a method of treating type 2 diabetes, insulin resistance, syndrome X, hyperinsulinaemia, hyperglucagonaemia, cardiac ischaemia or obesity in a warm-blooded animal, such as man, in need of such treatment which comprises administering to said animal an effective amount of a compound of formula (1).

According to this further feature of this aspect of the invention there is provided a method of treating type 2 diabetes in a warm-blooded animal, such as man, in need of such treatment which comprises administering to said animal an effective amount of a compound of formula (1).

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

In addition to their use in therapeutic medicine, the compounds of formula (1) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non-limiting examples in which, unless stated otherwise:
(i) temperatures are given in degrees Celsius (° C.); operations were carried out at room or ambient temperature, that is, at a temperature in the range of 18–25° C. and under an atmosphere of an inert gas such as argon;
(ii) organic solutions were dried over anhydrous magnesium sulphate; evaporation of solvent was carried out using a rotary evaporator under reduced pressure (600–4000 Pascals; 4.5–30 mmHg) with a bath temperature of up to 60° C.;
(iii) chromatography means flash chromatography on silica gel; thin layer chromatography (TLC) was carried out on silica gel plates; where a Bond Elut column is referred to, this means a column containing 10 g or 20 g or 50 g of silica of 40 micron particle size, the silica being contained in a 60 ml disposable syringe and supported by a porous disc, obtained from Varian, Harbor City, Calif., USA under the name "Mega Bond Elut SI"; "Mega Bond Elut" is a trademark; where a Biotage cartridge is referred to this means a cartridge containing KP-SIL™ silica, 60μ, particle size 32–63 mM, supplied by Biotage, a division of Dyax Corp., 1500 Avon Street Extended, Charlottesville, Va. 22902, USA;
(iv) in general, the course of reactions was followed by TLC and reaction times are given for illustration only;
(v) yields are given for illustration only and are not necessarily those which can be obtained by diligent process development; preparations were repeated if more material was required;
(vi) where given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$\delta_6$) as solvent unless otherwise indicated, other solvents (where indicated in the text) include deuterated chloroform $CDCl_3$;
(vii) chemical symbols have their usual meanings; SI units and symbols are used;
(viii) reduced pressures are given as absolute pressures in Pascals (Pa); elevated pressures are given as gauge pressures in bars;
(ix) solvent ratios are given in volume: volume (v/v) terms;
(x) The following abbreviations are used:
SM starting material;
EtOAc ethyl acetate;
MeOH methanol;
EtOH ethanol;
DCM dichloromethane;
HOBT 1-hydroxybenzotriazole;
DIPEA di-isopropylethylamine;
EDCI 1-ethyl-3-(3-dimethylaminopropyl)carbodi-imide hydrochloride;
$Et_2O$ diethyl ether;
THF tetrahydrofuran;
DMF N,N-dimethylformamide;
HATU O-(7-Azabenzotriazol-1-yl)-N,N,N',N'-tetramethyluroniumhexafluorophosphate
DMAP 4-dimethylaminopyridine
TBAF tetrabutylammonium fluoride
TFA trifluoroacetic acid Certain intermediates described hereinafter within the scope of the invention may also possess useful activity, and are provided as a further feature of the invention.

Example 1

5-Chloro-N-[1-(methoxycarbonylmethyl)-2-oxo-1,2,3,4-tetrahydroquinolin-3-yl]-1H-indole-2-carboxamide

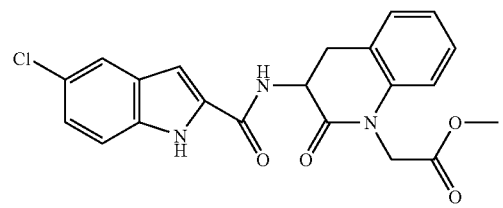

5-Chloro-1H-indole-2-carboxylic acid (493 mg, 2.52 mmol), HOBT (340 mg, 2.52 mmol), DCM (100 mL) and finally EDCI (483 mg, 2.52 mmol) were added to methyl 2-(3-amino-2-oxo-3,4-dihydroquinolin-1(2H)-yl)acetate (Method 1; 590 mg, 2.52 mmol) and the reaction was stirred for 18 h. The reaction was then diluted with water (50 mL) and stirred vigorously for 30 min. The resultant precipitate was filtered and washed with $Et_2O$ (2×20 mL). After filtration the resultant solid was then triturated with refluxing $Et_2O$ (25 mL) and after cooling the title compound (608 mg, 59%) was collected again by filtration as a white solid.

$^1$H NMR 3.11 (dd, 1H), 3.25 (app. t, 1H), 3.69 (s, 3H), 4.67 (d, 1H), 4.83 (m, 2H), 7.09 (m, 2H), 7.23 (m, 2H), 7.32 (m, 2H), 7.47 (d, 1H), 7.76 (s, 1H), 8.92 (d, 1H), 11.83 (s, 1H); MS m/z MNa$^+$ 434, 436.

Example 2

N-[1-(Carboxymethyl)-2-oxo-1,2,3,4-tetrahydroquinolin-3-yl]-5-chloroindole-2-carboxamide

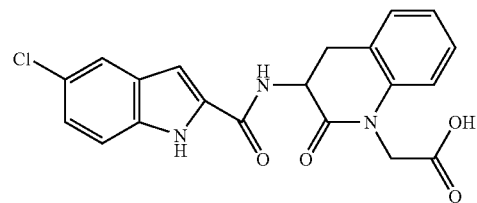

LiOH (91.5 g, 2.18 mmol) in $H_2O$ (2 mL) was added to a stirring solution of 5-chloro-N-[1-(methoxycarbonylmethyl)-2-oxo-1,2,3,4-tetrahydroquinolin-3-yl]-1H-indole-2-carboxamide (Example 1; 557 mg, 1.09 mmol) in THF (11 mL) and the reaction was stirred for 3 h. The reaction was quenched by addition of 1M aqueous HCl (40 mL) and EtOAc (60 mL) and the organic layer was dried (MgSO$_4$), filtered and evaporated. The resultant white foam was triturated with hot $Et_2O$ (20 mL) cooled, filtered, dried and collected by filtration to afford the title compound (500 mg, 92%) as a white solid.

$^1$H NMR 3.08 (dd, 1H), 3.25 (app. t, 1H), 4.53 (d, 1H), 4.77 (m, 2H), 7.06 (m, 2H), 7.24 (m, 4H), 7.45 (d, 1H), 7.74 (s, 1H), 8.90 (d, 1H), 11.83 (s, 1H); MS m/z MH$^+$ 398, 400.

Example 3

5-Chloro-N-(2-oxo-1,2,3,4-tetrahydroquinolin-3-yl)-1H-indole-2-carboxamide

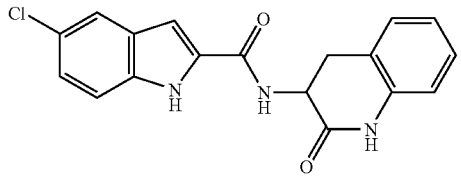

5-Chloroindole-2-carboxylic acid (196 mg, 1 mmol) was dissolved in DMF (5 mL) containing 3-amino-3,4-dihydroquinolin-2(1H)-one hydrochloride (*J. Med. Chem.* 28, 1985, 1511–16; 162 mg, 1 mmol), EDCI (192 mg, 1 mmol) and HOBT (135 mg, 1 mmol). The mixture was stirred at ambient temperature for approximately 18 h before being partitioned between water and EtOAc. The organics were washed with water, saturated aqueous NaHCO$_3$, saturated brine and dried over MgSO$_4$; then filtered and evaporated to afford the title compound (212 mg, 66%) as an amorphous white solid.

$^1$H NMR 3.13 (m, 2H), 4.77 (m, 1H), 6.92 (d, 1H), 6.96 (t, 1H), 7.21 (m, 4H), 7.47 (d, 1H), 7.76 (d, 1H), 8.80 (d, 1H), 10.38 (s, 1H), 11.84 (s, 1H); MS m/z MH$^+$ 340, 342.

Example 4

5-Chloro-N-[{2-oxo-1-[2-oxo-2-(pyridin-2-ylamino)ethyl]-1,2,3,4-tetrahydroquinolin-3-yl}-1H-indole-2-carboxamide

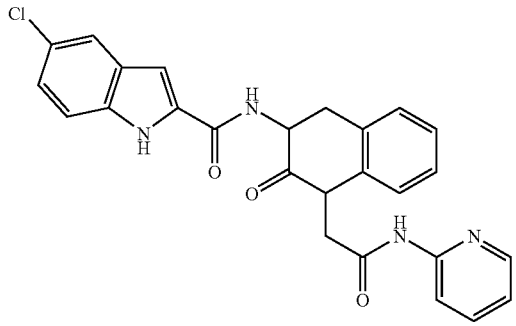

N-(1-{2-[(2,5-Dioxopyrrolidin-1-yl)oxy]-2-oxoethyl}-2-oxo-1,2,3,4-tetrahydroquinolin-3-yl)-5-methyl-1H-indole-2-carboxamide (Method 2; 188 mg, 0.38 mmol) and 2-aminopyridine (108 mg, 1.14 mmol) were dissolved in 1-methyl-2-pyrrolidinone (0.4 mL) and heated to 150° C. for 3 hours. On cooling the mixture was poured into H$_2$O (10 mL) and the resultant solid filtered off and dried under reduced pressure. The residue was purified by column chromatography (DCM to DCM:THF (4:1)) to give a yellow solid. The solid was triturated with refluxing Et$_2$O (25 mL), filtered, washed with Et$_2$O (25 mL) then hexane (25 mL) to afford the title compound as an off white solid.

$^1$H NMR 3.11 (dd, 1H), 3.28 (app. t, 1H), 4.73 (d, 1H), 4.87 (m, 1H), 5.00 (d, 1H), 7.11 (m, 3H), 7.27 (m, 4H), 7.46 (d, 1H), 7.63–7.71 (m, 2H), 8.00 (d, 1H), 8.34 (d, 1H), 8.91 (d, 1H), 10.81 (br. s, 1H), 11.85 (br. s, 1H); MS m/z (M–H)$^-$ 472, 474.

Example 5

5-Chloro-N-[1-[2-(methylthio)ethyl]-2-oxo-1,2,3,4-tetrahydroquinolin-3-yl]-1H-indole-2-carboxamide

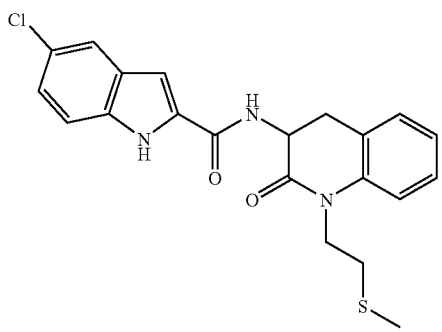

Sodium thiomethoxide (280 mg, 4.00 mmol) and KI (10 mg, 0.06 mmol) were added to a soluton of 5-chloro-N-[1-(2-chloroethyl)-2-oxo-1,2,3,4-tetrahydroquinolin-3-yl]-1H-indole-2-carboxamide (Method 3; 1.07 g, 2.67 mmol) in DMF (10 mL) under an inert atmosphere and heated at 80° C. for 2 hours. On cooling the mixture was diluted with EtOAc (100 mL), washed with water (20 mL), dried (Na$_2$SO$_4$), filtered and evaporated. The residue was purified by column chromatography (DCM to DCM:THF (2:23)) to give a white solid. The solid was triturated with refluxing Et$_2$O (20 mL) and the solid filtered, washed with Et$_2$O (10 mL) then hexane (10 mL) to afford the title compound (410 mg, 37%) as an off white solid.

$^1$H NMR 2.13 (s, 3H), 2.70 (t, 2H), 3.06 (dd, 1H), 3.18 (app. t, 1H), 4.15 (m, 2H), 4.77 (m, 1H), 7.08 (t, 1H), 7.23 (m, 3H), 7.33 (m, 2H), 7.46 (d, 1H), 7.75 (d, 1H), 8.92 (dd, 1H), 11.88 (br. s, 1H); MS m/z (M–H)$^-$ 412, 414

Example 6

5-Chloro-N-{1-[2-(methylsulphinyl)ethyl]-2-oxo-1,2,3,4-tetrahydroquinolin-3-yl}-1H-indole-2-carboxamide and

Example 7

5-Chloro-N-{1-[2-(methylsulphonyl)ethyl]-2-oxo-1,2,3,4-tetrahydroquinolin-3-yl}-1H-indole-2-carboxamide

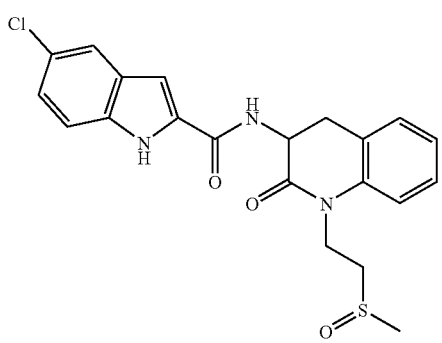

-continued

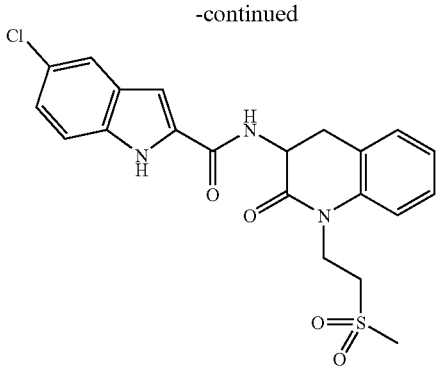

Oxone (701 mg, 1.14 mmol) in H₂O (12 mL) was added to 5-chloro-N-{1-[2-(methylthio)ethyl]-2-oxo-1,2,3,4-tetrahydroquinolin-3-yl}-1H-indole-2-carboxamide (Example 5; 355 mg, 0.86 mmol) in MeOH (12 mL) and stirred for 18 hours. The mixture was diluted with EtOAc (100 mL) washed with saturated NaHCO₃ (20 mL), dried (Na₂SO₄), filtered and evaporated. The residue was purified by column chromatography (DCM to DCM:THF (3:2) then DCM:MeOH (4:1)) to give 2 yellow solids. Each solid was triturated with refluxing Et₂O (25 mL) and the solids filtered, washed with Et₂O (25 mL) then hexane (25 mL) to afford 5-chloro-N-{1-[2-(methylsulphinyl)ethyl]-2-oxo-1,2,3,4-tetrahydroquinolin-3-yl}-1H-indole-2-carboxamide (125 mg, 34%) and 5-chloro-N-{1-[2-(methylsulphonyl)ethyl]-2-oxo-1,2,3,4-tetrahydroquinolin-3-yl}-1H-indole-2-carboxamide (95 mg, 25%) as white solids.

5-Chloro-N-{1-[2-(methylsulphinyl)ethyl]-2-oxo-1,2,3,4-tetrahydroquinolin-3-yl}-1H-indole-2-carboxamide ¹H NMR 2.63 (s, 3H), 3.08 (m, 4H), 4.32 (m, 2H), 4.77 (m, 1H), 7.10 (t, 1), 7.28 (m, 5H), 7.46 (d, 1H), 7.75 (s, 1H), 8.86 (dd, 1H), 11.85 (br. s, 1H); MS m/z (M−H)⁻ 428, 430.

5-Chloro-N-{1-[2-(methylsulphonyl)ethyl]-2-oxo-1,2,3,4-tetrahydroquinolin-3-yl}-1H-indole-2-carboxamide ¹H NMR 3.08 (m, 5H), 3.47 (m, 2H), 4.36 (t, 2H), 4.77 (m, 1H), 7.10 (t, 1), (m, 3H), 7.35 (m, 2H), 7.46 (d, 1H), 7.75 (s, 1H), 8.86 (dd, 1H), 11.85 (br. s, 1H); MS m/z (M+Na)⁺ 468, 470.

Example 8

5-Chloro-N-{2-oxo-1-[2-oxo-2-(1,3,4-thiadiazol-2-ylamino)ethyl]-1,2,3,4-tetrahydroquinolin-3-yl}-1H-indole-2-carboxamide

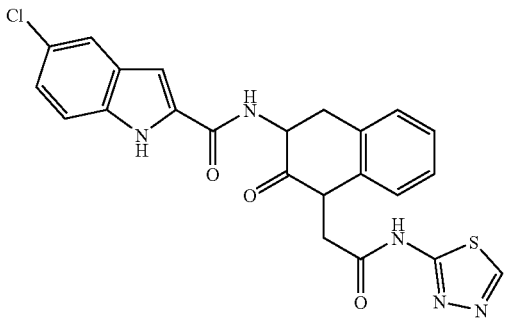

N-[1-(Carboxymethyl)-2-oxo-1,2,3,4-tetrahydroquinolin-3-yl]-5-chloroindole-2-carboxamide (Example 2; 250 mg, 0.629 mmol), HOBT (85 mg, 0.629 mmol) and amine (1.89 mmol) were mixed together and dissolved in DMF (3 mL). EDCI (363 mg, 1.89 mmol) was added in one portion and the sides of the tubes rinsed down with DMF (2 mL). After stirring overnight at room temperature the reaction was poured into water (25 mL) and the title compound filtered off as a solid. Analysis was by 1 cms using the following conditions:—
Phenomenex Synergi Column 50×2.0 mm 4u.
Acetonitrile (B)/Water (A) eluent
Flow rate 1.2 mls min-1
Gradient:—1.0% B to 95% B over 4.5 mins
Wavelength 254 n.m.

| | Ret. time | MW | MH+ | MH− |
|---|---|---|---|---|
| Example 8 | 2.75 | 480 | | 479 |

Examples 9–22

The following examples were synthesized by an analogous method to Example 8:

Example 9: 5-chloro-N-(1-{2-[(6-methylpyridin-2-yl)amino]-2-oxoethyl}-2-oxo-1,2,3,4-tetrahydroquinolin-3-yl)-1H-indole-2-carboxamide Example 10: 5-chloro-N-{2-oxo-1-[2-oxo-2-(pyridin-3-ylamino)ethyl]-1,2,3,4-tetrahydroquinolin-3-yl}-1H-indole-2-carboxamide Example 11: 5-chloro-N-(1-{2-[(5-methyl-1,3,4-thiadiazol-2-yl)amino]-2-oxoethyl}-2-oxo-1,2,3,4-tetrahydroquinolin-3-yl)-1H-indole-2-carboxamide Example 12: 5-chloro-N-(1-{2-[(5-ethyl-1,3,4-thiadiazol-2-yl)amino]-2-oxoethyl}-2-oxo-1,2,3,4-tetrahydroquinolin-3-yl)-1H-indole-2-carboxamide Example 13: 5-chloro-N-(1-{2-[(4-cyano-1H-pyrazol-3-yl)amino]-2-oxoethyl}-2-oxo-1,2,3,4-tetrahydroquinolin-3-yl)-1H-indole-2-carboxamide Example 14: 5-chloro-N-(1-{2-[(4-methyl-1,3-thiazol-2-yl)amino]-2-oxoethyl}-2-oxo-1,2,3,4-tetrahydroquinolin-3-yl)-1H-indole-2-carboxamide Example 15: 5-chloro-N-(1-{2-[(6-chloropyridin-3-yl)amino]-2-oxoethyl}-2-oxo-1,2,3,4-tetrahydroquinolin-3-yl)-1H-indole-2-carboxamide Example 16: 5-chloro-N-(1-{2-[(3-hydroxypyridin-2-yl)amino]-2-oxoethyl}-2-oxo-1,2,3,4-tetrahydroquinolin-3-yl)-1H-indole-2-carboxamide Example 17: 5-chloro-N-(2-oxo-1-{2-oxo-2-[(pyridin-2-ylmethyl)amino]ethyl}-1,2,3,4-tetrahydroquinolin-3-yl)-1H-indole-2-carboxamide Example 18: 5-chloro-N-{2-oxo-1-[2-oxo-2-(pyridin-4-ylamino)ethyl]-1,2,3,4-tetrahydroquinolin-3-yl}-1H-indole-2-carboxamide Example 19: 5-chloro-N-(1-{2-[(1-methyl-1H-pyrazol-5-yl)amino]-2-oxoethyl}-2-oxo-1,2,3,4-tetrahydroquinolin-3-yl)-1H-indole-2-carboxamide Example 20: 5-chloro-N-(1-{2-[(1,3-dimethyl-1H-pyrazol-5-yl)amino]-2-oxoethyl}-2-oxo-1,2,3,4-tetrahydroquinolin-3-yl)-1H-indole-2-carboxamide Example 21: 5-chloro-N-(2-oxo-1-{2-oxo-2-[(pyrazin-2-ylmethyl)amino]ethyl}-1,2,3,4-tetrahydroquinolin-3-yl)-1H-indole-2-carboxamide Example 22: 5-chloro-N-(1-{2-[(6-fluoropyridin-3-yl)amino]-2-oxoethyl}-2-oxo-1,2,3,4-tetrahydroquinolin-3-yl)-1H-indole-2-carboxamide

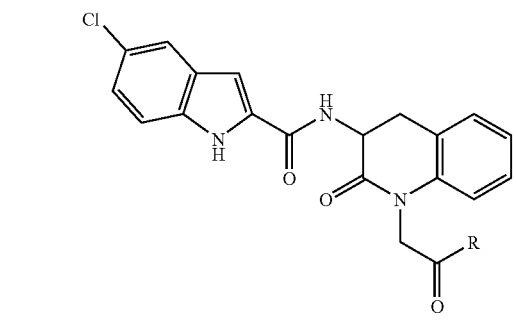

| Example | R | Ret. time | MW | MH+ | MH− |
|---|---|---|---|---|---|
| 9 | NH–(6-methylpyridin-2-yl) | 3.08 | 487 | 488 | |
| 10 | NH–(pyridin-3-yl) | 2.46 | 473 | 474 | |
| 11 | NH–(5-methyl-1,3,4-thiadiazol-2-yl) | 2.28 | 494 | 495 | |
| 12 | NH–(5-ethyl-1,3,4-thiadiazol-2-yl) | 2.52 | 508 | 509 | |
| 13 | NH–(4-cyano-1H-pyrazol-3-yl) | 2.54 | 487 | | 486 |
| 14 | NH–(4-methylthiazol-2-yl) | 2.52 | 493 | 494 | |
| 15 | NH–(6-chloropyridin-3-yl) | 2.56 | 507 | | 506 |
| 16 | NH–(3-hydroxypyridin-2-yl) | 2.09 | 489 | 490 | |
| 17 | NH–CH2–(pyridin-2-yl) | 1.82 | 487 | 488 | |

-continued

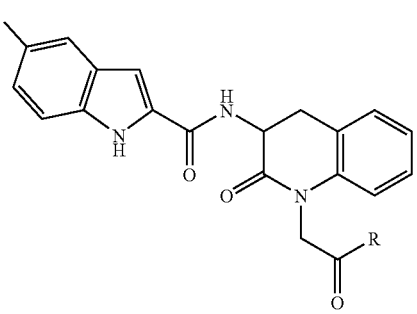

| Example | R | Ret. time | MW | MH+ | MH− |
|---|---|---|---|---|---|
| 18 | NH–(pyridin-4-yl) | 1.58 | 473 | 474 | |
| 19 | NH–(1-methyl-1H-pyrazol-5-yl) | 2.2 | 476 | | 477 |
| 20 | NH–(1,3-dimethyl-1H-pyrazol-5-yl) | 2.26 | 490 | 491 | |
| 21 | NH–CH2–(pyrazin-2-yl) | 2.12 | 488 | 489 | |
| 22 | NH–(6-fluoropyridin-3-yl) | 2.99 | 491 | 492 | |

Examples 23–35

The following examples were synthesized by an analogous method to Example 8 with additional purification by reverse phase prep HPLC using the following conditions:
Column=Phenomenex Luna 10u C18.
Flow rate=25 mL/min
Run time=9 mins
Eluent H₂O (0.1% formic acid): CH₃CN (0.1% formic acid) (Gradient (95:5) to (0:100).

Example 23: 5-chloro-N-(1-{2-[(2-hydroxypyrimidin-4-yl)amino]-2-oxoethyl}-2-oxo-1,2,3,4-tetrahydroquinolin-3-yl)-1H-indole-2-carboxamide Example 24: 5-chloro-N-{2-oxo-1-[2-oxo-2-(pyrimidin-4-ylamino)ethyl]-1,2,3,4-tetrahydroquinolin-3-yl}-1H-indole-2-carboxamide Example 25: 5-chloro-N-(1-{2-[(1-ethyl-1H-pyrazol-5-yl)amino]-2-oxoethyl}-2-oxo-1,2,3,4-tetrahydroquinolin-3-yl)-1H-indole-2-carboxamide Example 26: 5-chloro-N-(2-oxo-1-{2-oxo-2-[(5-oxo-4,5-dihydro-1H-pyrazol-3-yl)amino]ethyl}-1,2,3,4-tetrahydroquinolin-3-yl)-1H-indole-2-carboxamide Example 27: 5-chloro-N-(1-{2-[(4-hydroxypyrimidin-2-yl)amino]-2-oxoethyl}-2-oxo-1,2,3,4-tetrahydroquinolin-3-yl)-1H-indole-2-carboxamide Example 28: 5-chloro-N-(1-{2-[(3-methylpyridin-2-yl)amino]-2-oxoethyl}-2-oxo-1,2,3,4-tetrahydroquinolin-3-yl)-1H-indole-2-carboxamide Example 29: 5-chloro-N-(1-{2-[(6-chloropyridazin-3-yl)amino]-2-oxoethyl}-2-oxo-1,2,3,4-tetrahydroquinolin-3-yl)-1H-indole-2-carboxamide Example 30: 5-chloro-N-(1-{2-[(1H-imidazol-2-ylmethyl)amino]-2-oxoethyl}-2-oxo-1,2,3,4-tetrahydroquinolin-3-yl)-1H-indole-2-carboxamide Example 31: 5-chloro-N-(1-{2-[(1-methyl-1H-pyrazol-3-yl)amino]-2-oxoethyl}-2-oxo-1,2,3,4-tetrahydroquinolin-3-yl)-1H-indole-2-carboxamide Example 32: 5-chloro-N-{2-oxo-1-[2-oxo-2-(2H-tetrazol-5-ylamino)ethyl]-1,2,3,4-tetrahydroquinolin-3-yl}-1H-indole-2-carboxamide Example 33: 5-chloro-N-(1-{2-[(3-ethyl-1H-pyrazol-5-yl)amino]-2-oxoethyl}-2-oxo-1,2,3,4-tetrahydroquinolin-3-yl)-1H-indole-2-carboxamide Example 34: 5-chloro-N-(1-{2-[(5-fluoropyridin-2-yl)amino]-2-oxoethyl}-2-oxo-1,2,3,4-tetrahydroquinolin-3-yl)-1H-indole-2-carboxamide Example 35: N-(1-{2-[(6-bromopyridin-3-yl)amino]-2-oxoethyl}-2-oxo-1,2,3,4-tetrahydroquinolin-3-yl)-5-chloro-1H-indole-2-carboxamide

| Example | R | Ret. time | MW | MH+ | MH− |
|---|---|---|---|---|---|
| 23 | 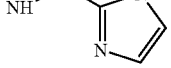 | 2.69 | 490 | 491 | |
| 24 | 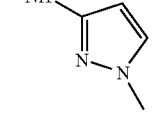 | 2.89 | 474 | 475 | |
| 25 | 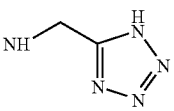 | 2.97 | 490 | 491 | |
| 26 | 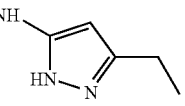 | 2.75 | 478 | | 477 |
| 27 | 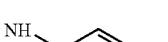 | 2.71 | 490 | 491 | |
| 28 | 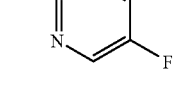 | 2.74 | 487 | 488 | |
| 29 | 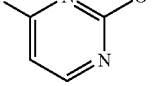 | 3.19 | 508 | 509 | |
| 30 | 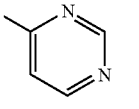 | 2.13 | 476 | 477 | |
| 31 | 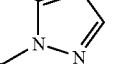 | 2.91 | 476 | 477 | |
| 32 | 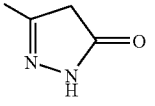 | 2.73 | 478 | 479 | |
| 33 | 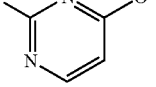 | 3.43 | 490 | 491 | |
| 34 | 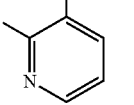 | 3.26 | 491 | 492 | |
| 35 | 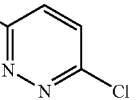 | 2.28 | 552 | 553 | |

Example 36

5-Chloro-N-[1-(2-hydroxyethyl)-2-oxo-1,2,3,4-tetrahydroquinolin-3-yl]-1H-indole-2-carboxamide

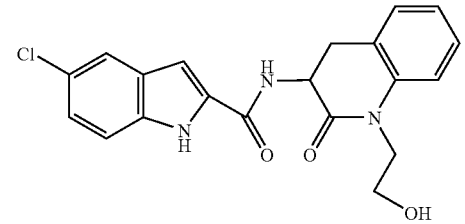

Triethylamine (0.168 mL, 1.21 mmol) then ethyl chloroformate (0.115 mL, 1.21 mmol) were added to N-[1-(carboxymethyl)-2-oxo-1,2,3,4-tetrahydroquinolin-3-yl]-5-chloroindole-2-carboxamide (Example 2, 437 mg, 1.10 mmol) in anhydrous THF (10 mL) at 0° C. followed by stirring for 1 h. LiBH$_4$ (2.0 M in THF, 0.69 mL, 1.37 mmol) was added slowly and the mixture stirred for a further 30 min. The reaction was carefully quenched with 1M HCl (50 mL) and EtOAc (100 mL) and the organic layer was further washed with sat. aqueous NaHCO$_3$ (30 mL), brine (30 mL), dried (MgSO$_4$), filtered and evaporated. The residue was triturated with refluxing Et$_2$O (10 mL) and after cooling the solid was filtered and dried to afford the title compound (325 mg, 77%) a white solid.

¹H NMR 3.05 (dd, 1H), 3.17 (t, 1H), 3.61 (m, 2H), 3.93 (m, 1H), 4.03 (m, 1H), 4.77 (m, 1H), 4.86 (t, 1H), 7.05 (m, 1H), 7.22 (m, 2H), 7.31 (m, 3H), 7.45 (d, 1H), 7.75 (d, 1H), 8.83 (d, 1H), 11.85 (s, 1H); MS m/z 384, 386

Example 37

5-Chloro-N-{1-[(2,2-dimethyl-1,3-dioxan-5-yl)methyl]-2-oxo-1,2,3,4-tetrahydroquinolin-3-yl}-1H-indole-2-carboxamide

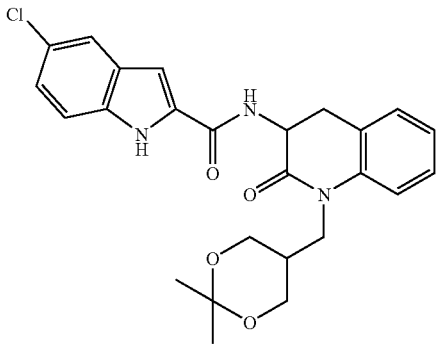

Following a standard amide coupling procedure analogous to Example 1, using 3-amino-1-[(2,2-dimethyl-1,3-dioxan-5-yl)methyl]-3,4-dihydroquinolin-2(1H)-one (Method 4) as the amine and 5-chloroindole-2-carboxylic acid as the acid afforded the title compound (85%) as a white solid.

¹H NMR 1.34 (s, 3H₁), 1.39 (s, 3H), 2.00 (m, 1H), 3.08 (dd, 1H), 3.20 (t, 1H), 3.75 (m, 2H), 3.83 (m, 3H), 4.20 (dd, 1H), 4.75 (quin, 1H), 7.06 (t, 1H), 7.24 (m, 2H), 7.30 (m, 3H), 7.45 (d, 1H), 7.73 (s, 1H), 8.82 (d, 1H), 11.86 (s, 1H); MS m/z 468, 470.

Example 38

5-Chloro-N-{1-[3-hydroxy-2-(hydroxymethyl)propyl]-2-oxo-1,2,3,4-tetrahydroquinolin-3-yl}-1H-indole-2-carboxamide

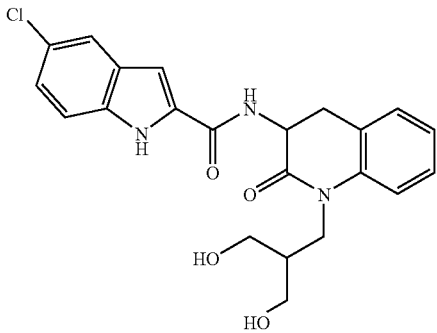

6M aqueous HCl (2.34 mL) was added to 5-chloro-N-{1-[(2,2-dimethyl-1,3-dioxan-5-yl)methyl]-2-oxo-1,2,3,4-tetrahydroquinolin-3-yl}-1H-indole-2-carboxamide (Example 37; 540 mg, 1.16 mmol) in THF (19 mL) and the reaction was stirred for 1 h. The reaction was quenched by addition of triethylamine (1.5 mL) and the reaction was diluted with water (20 mL) and EtOAc (40 mL). The organic layer was separated, dried (MgSO₄), filtered and evaporated. The residue was triturated with hot Et₂O (15 mL) and after cooling was filtered and dried to afford the title compound (421 mg, 85%) as white solid.

¹H NMR 1.90 (m, 1H), 3.13 (m, 2H), 3.39 (m, 3H), 3.51 (m, 1H), 3.86 (dd, 1H), 4.08 (dd, 1H), 4.38 (t, 1H), 4.50 (t, 1H), 4.73 (quin, 1H), 7.04 (t, 1H), 7.18 (m, 2H), 7.29 (m, 3H), 7.43 (d, 1H), 7.72 (s, 1H), 8.80 (d, 1H), 11.82 (s, 1H); MS m/z 428, 430.

Example 39

5-Chloro-N-[1-(2,3-dihydroxypropyl)-2-oxo-1,2,3,4-tetrahydroquinolin-3-yl]-1H-indole-2-carboxamide

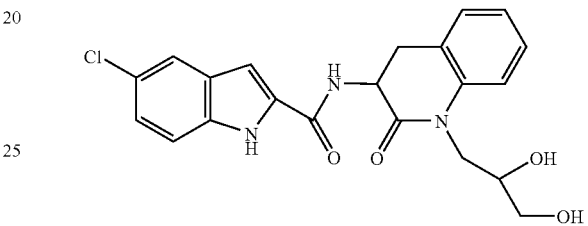

The procedure of Example 37 was followed using 3-amino-1-[(2,2-dimethyl-1,3-dioxolan-4-yl)methyl]-3,4-dihydroquinolin-2(1H)-one (Method 5) as amine and 5-Chloro-1H-indole-2-carboxylic acid as the acid component, to give the title compound as a white solid which was used without purification and subjected to acid catalysed hydrolysis according to the method used for Example 38 gave the title compound (90%) as a white solid.

¹H NMR 3.10 (m, 2H), 3.37 (m, 2H), 3.90 (m, 3H), 4.71 (m, 3H), 7.04 (t, 1H), 7.23 (m, 5H), 7.46 (d, 1H), 7.72 (s, 1H), 8.81 (t, 1H), 11.83 (s, 1H); MS m/z 414

Example 40

5-Chloro-N-[1-(3-hydroxy-2-oxopropyl)-2-oxo-1,2,3,4-tetrahydroquinolin-3-yl]-1H-indole-2-carboxamide

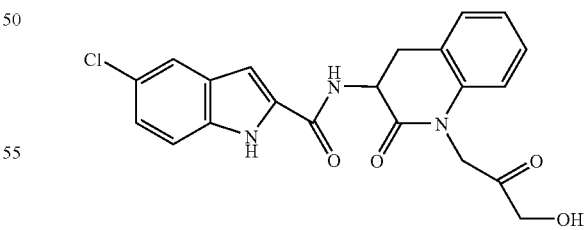

Dess-Martin Periodinane (120 mg, 0.28 mmol) was added to a stirring solution of N-[1-(3-{[tert-butyl(dimethyl)silyl]oxy}-2-hydroxypropyl)-2-oxo-1,2,3,4-tetrahydroquinolin-3-yl]-5-chloro-1H-indole-2-carboxamide (Method 6, 74 mg, 0.14 mmol) in DCM and the reaction was stirred for 2 hours. The reaction was quenched by addition of sat. aqueous NaHCO₃ (20 mL) and EtOAc (40 mL) and the organic layer was separated and further washed with acidified (pH 0)

sodium metabisulfite (10 mL) and the organic layer was dried (MgSO$_4$), filtered and evaporated. Purification by column chromatography (1:19 MeOH:DCM) afforded the title compound (18 mg, 31%) as a white solid.

$^1$H NMR 3.10 (dd, 1H), 3.27 (m, 1H), 4.27 (d, 2H), 4.83 (m, 2H), 5.09 (d, 1H), 5.41 (t, 1H), 6.90 (d, 1H), 7.07 (t, 1H), 7.27 (m, 4H), 7.47 (d, 1H), 7.74 (s, 1H), 8.89 (d, 1H), 11.85 (s, 1H); MS m/z 412, 414.

Example 41

5-Chloro-N-{1-[(2R)-2,3-dihydroxypropyl]-2-oxo-1,2,3,4-tetrahydroquinolin-3-yl}-1H-indole-2-carboxamide

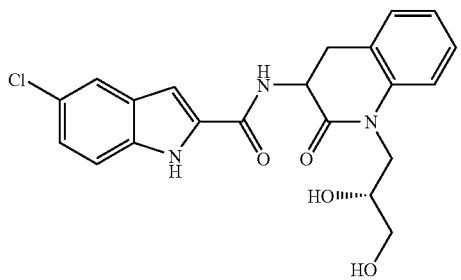

6N HCl was added dropwise to a solution of 5-chloro-N-(1-{[(4R)-2,2-dimethyl-1,3-dioxolan-4-yl]methyl}-2-oxo-1,2,3,4-tetrahydroquinolin-3-yl)-1H-indole-2-carboxamide (Method 7, 500 mg, 1.1 mmol) and the reaction was stirred at ambient temperature for 2 hours. Saturated NaHCO$_3$ solution was added cautiously until the reaction mixture was at pH 8, the mixture was extracted with EtOAc (2×20 mL), the combined organic phases dried (MgSO$_4$) and the volatiles removed under reduced pressure to give the title compound (450 mg, 99%) as a yellow solid.

$^1$H NMR 3.10 (m, 1H), 3.25 (app. t, 1H), 3.45 (m, 2H), 3.90 (m, 2H), 4.13 (m, 1H), 4.70 (m, 1H), 4.83 (m, 1H), 4.95 (dd, 1H), 7.43 (m, 8H), 8.92 (dd, 1H), 11.92 (s, 1H); MS m/z (M+Na) 436, 438.

Example 42

5-Chloro-N-(1-{2-[(methylsulfonyl)amino]ethyl}-2-oxo-1,2,3,4-tetrahydroquinolin-3-yl)-1H-indole-2-carboxamide

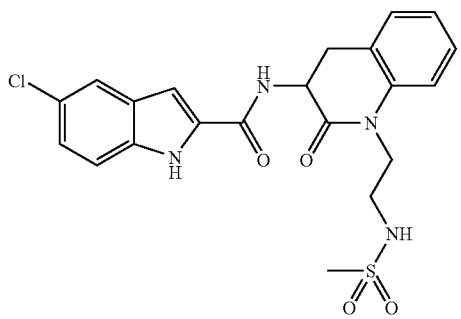

Triethylamine (80 μL, 0.6 mmol) was added to a stirred suspension of N-[1-(2-aminoethyl)-2-oxo-1,2,3,4-tetrahydroquinolin-3-yl]-5-chloro-1H-indole-2-carboxamide trifluoroacetate (Method 9, 150 mg, 0.3 mmol) and methanesulfonyl chloride (25 μL, 0.33 mmol) in anhydrous DCM (5 mL) at 0° C. The reaction was stirred at 0° C. for 30 mins, then warmed and stirred at ambient temperature for 30 mins. The reaction was poured into water (10 mL) and the layers were separated. The organic phase was washed with 1 N HCl (10 mL), brine (15 mL) and dried (MgSO$_4$). The volatiles were removed by evaporation under reduced pressure to give a pale yellow solid (100 mg). Purification by column chromatography (7:3 EtOAc:isohexane, then EtOAc) gave the title compound (34 mg, 22%) as a colourless solid.

$^1$H NMR 2.93 (s, 3H), 3.15 (m, 4H), 4.05 (m, 2H), 4.78 (m, 1H), 7.28 (m, 8H), 7.75 (s, 1H), 8.83 (d, 1H); MS m/z (M+Na) 483, 485.

Example 43

N-{1-[2-(Acetylamino)ethyl]-2-oxo-1,2,3,4-tetrahydroquinolin-3-yl}-5-chloro-1H-indole-2-carboxamide

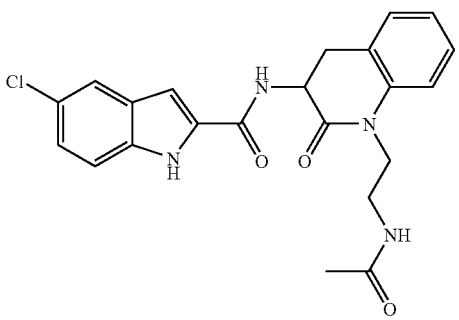

HOBT (27 mg, 0.2 mmol), acetic acid (12.5 μL, 0.22 mmol), DIPEA (35 μl, 0.2 mmol) and then EDCI (48 mg, 0.25 mmol) were added to a solution of N-[1-(2-aminoethyl)-2-oxo-1,2,3,4-tetrahydroquinolin-3-yl]-5-chloro-1H-indole-2-carboxamide trifluoroacetate (Method 9, 100 mg, 0.2 mmol) in DCM (2 mL) and THF (0.5 mL). The reaction was stirred for 90 mins at ambient temperature, diluted with EtOAc (5 mL), washed with 1 N NaOH (3 mL), 1 N HCl (3 mL), saturated aqueous NaHCO$_3$ solution (5 mL) and dried (MgSO$_4$). Column chromatography (7:3 to 8:2 EtOAc:isohexane) gave the title compound (40 mg, 47%) as a tan solid.

$^1$H NMR 1.23 (s, 3H), 3.15 (m, 2H), 4.30 (t, 2H), 4.75 (m, 1H), 3.95 (m, 2H), 7.33 (m, 8H); MS m/z (M+Na) 447, 448.

Example 44

5-Chloro-N-(2-oxo-1-{2-[(trifluoroacetyl)amino]ethyl}-1,2,3,4-tetrahydroquinolin-3-yl)-1H-indole-2-carboxamide

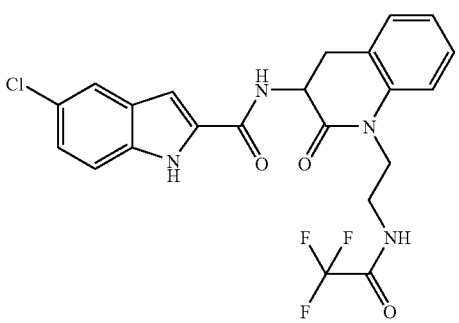

Sodium borohydride (98 mg, 2.6 mmol) was added cautiously to a stirred suspension of cobalt chloride hexahydrate (124 mg, 0.52 mmol), trifluoroacetic anhydride (70 µL, 0.52 mmol) and 5-chloro-N-[1-(cyanomethyl)-2-oxo-1,2,3,4-tetrahydroquinolin-3-yl]-1H-indole-2-carboxamide (Method 11, 100 mg, 0.26 mmol) in MeOH (4 mL) and THF (2 mL) at 0° C. The reaction was allowed to warm to ambient temperature, stirred for five days and then filtered through a pad of Celite, washing through with 9:1 MeOH:water (2×10 mL) and the filtrate evaporated under reduced pressure. The residue was taken up in EtOAc (20 mL), washed with saturated aqueous NaHCO$_3$ solution (10 mL), 1 N HCl (10 mL), brine (10 mL), dried (MgSO$_4$) and the volatiles removed under reduced pressure. Column chromatography (1:1 EtOAc:isohexane) gave the title compound (27 mg, 22%) as a pale yellow solid. $^1$H NMR 3.13 (m, 2H), 3.45 (br. m, 2H), 4.05 (m, 2H), 4.80 (m, 1H), 7.38 (m, 8H), 8.80 (d, 1H), 9.30 (s, 1H); MS m/z (M+Na) 501, 503.

Example 45

5-Chloro-N-[1-(3-hydroxypropyl)-2-oxo-1,2,3,4-tetrahydroquinolin-3-yl]-1H-indole-2-carboxamide

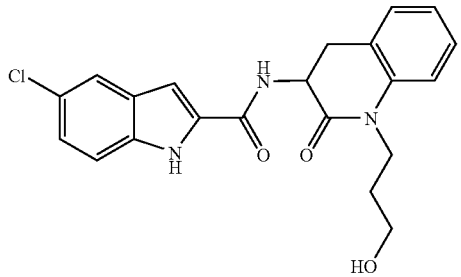

A 1 M solution of TBAF in THF (1 mL) was added dropwise to a solution of N-[1-(3-{[tert-butyl(dimethyl)silyl]oxy}propyl)-2-oxo-1,2,3,4-tetrahydroquinolin-3-yl]-5-chloro-1H-indole-2-carboxamide (Method 13, 400 mg, 0.78 mmol) in THF (5 mL). The reaction was stirred at ambient temperature for 24 h, partitioned between EtOAc (25 mL) and saturated aqueous NH$_4$Cl solution (20 mL), the layers separated and the organic phase dried (MgSO$_4$). The volatiles were removed under reduced pressure to give an off-white solid which was washed with water, isohexane, diethyl ether and dried under vacuum to give the title compound (234 mg, 75%) as an off-white solid.
$^1$H NMR 1.80 (m, 2H), 3.15 (m, 2H), 3.53 (m, 2H), 4.05 (m, 1H), 4.58 (t, 1H), 4.78 (m, 1H), 7.30 (m, 7H), 7.79 (s, 1H), 8.87 (d, 1H), 11.90 (s, 1H); MS m/z (M+Na) 420, 422.

Example 46

N-{1-[(2Z)-2-Amino-2-(hydroxyimino)ethyl]-2-oxo-1,2,3,4-tetrahydroquinolin-3-yl}-5-chloro-1H-indole-2-carboxamide

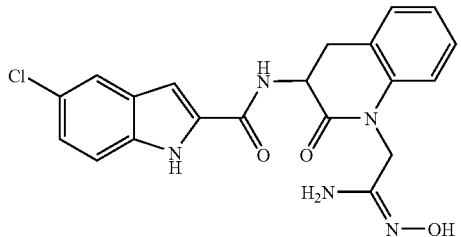

A solution hydroxylamine hydrochloride (147 mg, 2.11 mmol) in MeOH (4 mL) was added to a solution of sodium methoxide in methanol (0.5 M, 4.2 mL, 2.1 mmol) that had been further diluted with methanol (4 mL). After stirring for 10 minutes, THF (4 mL) was added followed by portionwise addition of 5-chloro-N-[1-(cyanomethyl)-2-oxo-1,2,3,4-tetrahydroquinolin-3-yl]-1H-indole-2-carboxamide (Method 11, 400 mg, 1.06 mmol). The reaction mixture was stirred at ambient temperature for 18 h, partitioned between EtOAc (80 mL) and diluted brine (80 mL), filtered and the layers of the filtrate separated. The organic phase was dried (Na$_2$SO$_4$) and the volatiles removed under reduced pressure to give the title material (191 mg, 44%) as a yellow solid.
$^1$H NMR 3.20 (m, 2H), 4.35 (d, 1H), 4.82 (d, 1H), 4.90 (m, 1H), 5.43 (br. s, 2H), 7.30 (m, 7H), 7.80 (s, 1H), 8.92 (d, 1H), 9.20 (s, 1H), 11.93 (s, 1H); MS m/z (M+Na) 434, 436.

Example 47

5-Chloro-N-(6-fluoro-2-oxo-1,2,3,4-tetrahydroquinolin-3-yl)-1H-indole-2-carboxamide

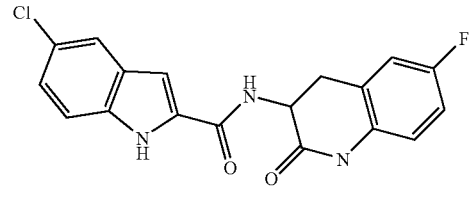

Triethylamine (184 µL, 1.32 mmol), HOBt (89 mg, 0.66 mmol), 3-amino-6-fluoro-3,4-dihydro-2(1H)-quinolinone monohydrochloride (CAS Reg. No: 82420-54-0) (143 mg, 0.66 mmol), and EDAC (127 mg, 0.66 mmol) were added to a solution of 5-chloroindole-2-carboxylic acid (129 mg, 0.66 mmol) in anhydrous DMF (3.5 mL). The reaction was stirred at ambient temperature for approximately 16 h, and then poured into water (50 mL). This was stirred vigorously for about 10 mins. and filtered. The collected precipitate was washed with water and dried in vacuum at 40° C., to give the title compound (200 mg, 85%) as an amorphous solid.
$^1$H NMR 3.15 (m, 2H), 4.76 (m, 1H), 8.92 (m, 1H), 7.06 (m, 1H), 7.17 (m, 1H), 7.20 (m, 2H), 7.46 (d, 1H), 7.76 (s, 1H), 8.80 (d, 1H), 10.40 (s, 1H), 11.86 (s, 1H); MS m/z 358, 360.

The following examples were made, by the process of Example 47, using 3-amino-3,4-dihydro-6-methoxy-2(1H)-quinolinone monohydrochloride (CAS Reg No: 35287-38-8) or 3-amino-3,4-dihydro-2(1H)-quinolinone (CAS Reg. No: 40615-17-6) and 5-chloroindole-2-carboxylic acid, as appropriately.

Example 48

5-Chloro-N-16-(methyloxy)-2-oxo-1,2,3,4-tetrahydroquinolin-3-yl]-1H-indole-2-carboxamide

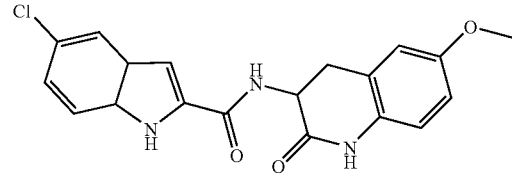

¹H NMR 3.06 (dd, 1H), 3.14 (t, 1H), 3.72 (s, 3H), 4.73 (m, 1H), 4.78 (m, 1H), 4.83 (s, 1H), 4.87 (m, 1H), 7.21 (m, 2H), 7.46 (d, 1H), 7.74 (s, 1H), 8.77 (d, 1H), 10.21 (s, 1H), 11.84 (s, 1H); MS m/z 370, 372.

Method 1

Methyl 2-[3-amino-2-oxo-3,4-dihydroquinolin-1(2H)-yl]acetate

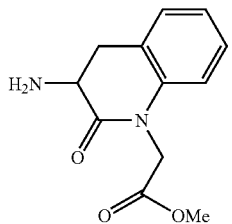

Sodium hydride (60% in oil, 2.52 g, 63.0 mmol) was added to 3-amino-3,4-dihydroquinolin-2(1 h)-one hydrochloride (J. Med. Chem. 28, 1985, 1511–16; 5.0 g, 25.2 mmol), in anhydrous DMF (100 mL) at 0° C. over a period of 5 min keeping the internal temperature at <10° C. The reaction was stirred for a further 30 min before addition of methyl bromoacetate (2.85 mL, 30.2 mmol), then stirred for a further 60 min. The reaction was quenched by addition of 1M aqueous HCl (5 mL) and the volatiles were removed by evaporation. The residue was dissolved in DCM (250 mL) and washed with sat. aqueous NaHCO₃ (100 mL) and the organic layer was dried (MgSO₄), filtered and evaporated to yield the title compound (5.89 g, 100%) as yellow paste which was used in the next reaction without further purification.

¹H NMR 2.21 (br. s, 2H), 2.78 (d, 1H), 2.97 (dd, 1H), 3.47 (dd, 1H), 3.67 (s, 3H), 4.55 (d, 1H), 4.78 (d, 1H), 6.96 (m, 2H), 7.23 (m, 2H); MS m/z MH₊ 235.

Method 2

N-(1-{2-[(2,5-Dioxopyrrolidin-1-yl)oxy]-2-oxoethyl}-2-oxo-1,2,3,4-tetrahydroquinolin-3-yl)-5-methyl-1H-indole-2-carboxamide

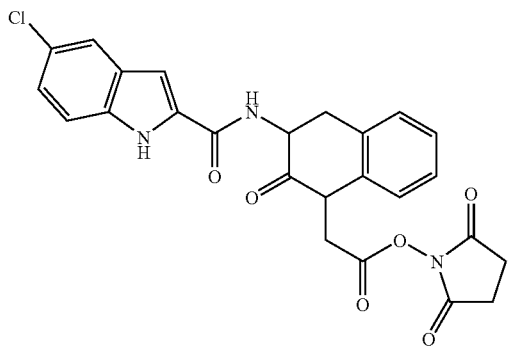

N-Hydroxysuccinimide (496 mg, 4.31 mmol) and EDCI (1.04 g, 5.38 mmol) were added to a suspension of N-[1-(carboxymethyl)-2-oxo-1,2,3,4-tetrahydroquinolin-3-yl]-5-chloroindole-2-carboxamide (Example 2, 1.71 g, 4.31 mmol)) in DCM (50 mL) and stirred for 18 hours. The suspension was evaporated and the residue partitioned between EtOAc:THF (4:1)(200 mL) and H₂O. The organic was dried (Na₂SO₄), filtered and evaporated. The solid was triturated with refluxing Et₂O (25 mL), filtered, washed with Et₂O (25 mL) then hexane (25 mL) to afford the title compound (2.08 g, 98%) as a pale brown powder.

¹H NMR 2.83 (s, 4H), 3.12 (dd, 1H), 3.27 (app. t, 1H), 4.85 (m, 1H), 5.15 (d, 1H), 5.34 (d, 1H), 7.12 (m, 2H), 7.22 (m, 2H), 7.35 (m, 2H), 7.46 (d, 1H), 7.75 (d, 1H), 8.96 (d, 1H), 11.86 (s, 1H); MS m/z (M–H)– 493, 495.

Method 3

5-Chloro-N-[1-(2-chloroethyl)-2-oxo-1,2,3,4-tetrahydroquinolin-3-yl]-1H-indole-2-carboxamide

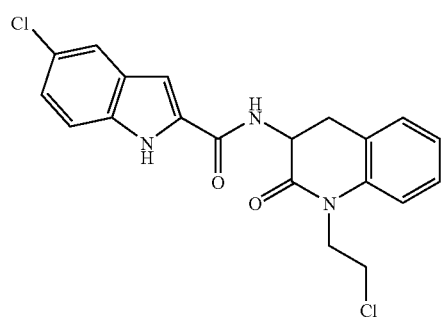

p-Toluenesulphonyl chloride (285 mg, 1.49 mmol) was added to a solution of 5-chloro-N-[1-(2-hydroxyethyl)-2-oxo-1,2,3,4-tetrahydroquinolin-3-yl]-1H-indole-2-carboxamide (Example 36; 286 mg, 0.75 mmol) in pyridine (2 mL) under an inert atmosphere and stirred at ambient temperature for 18 hours. The mixture was diluted with THF (10 mL) and EtOAc (50 mL) and washed with 1M HCl aq. (20 mL), water (20 mL), brine (20 mL), dried (MgSO₄), filtered and evaporated. The residue was purified by column chromatography (DCM to DCM:THF (9:1)) to afford the title compound (144 mg, 40%) as a yellow solid.

¹H NMR 3.11 (dd, 1H), 3.24 (app. t, 1H), 3.86 (t, 2H), 4.37 (m, 2H), 4.83 (m, 1H), 7.14 (t, 1H), 7.33 (m, 5H), 7.51 (d, 1H), 7.80 (d, 1H), 8.92 (d, 1H), 11.90 (br. s, 1H); MS m/z 402, 404.

Method 4

3-Amino-1-[(2,2-dimethyl-1,3-dioxan-5-yl)methyl]-3.4-dihydroquinolin-2(1H)-one

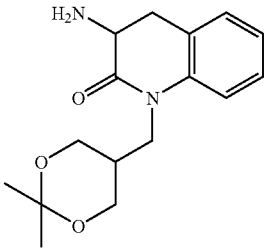

Sodium hydride (60% in oil, 1.60 g, 39.80 mmol) was added to 3-amino-3,4-dihydroquinolin-2(1H)-one hydrochloride (3.59 g, 18.09 mmol), in anhydrous DMF (50 mL) at 0° C. over a period of 10 min. The reaction was stirred for a further 30 min before addition of (2,2-dimethyl-1,3-dioxan-5-yl)methyl methanesulfonate [CAS registary number 131372-64-0] (4.05 g, 18.09 mmol) and the reaction has then heated to 60° C. for a period of 16 h. The reaction was then cooled and evaporated before addition of sat. aqueous NaHCO₃ (200 mL) and EtOAc (500 mL). The organic layer was then dried (MgSO₄), filtered and evaporated and the residue was purified by column chromatography (MeOH:DCM, 3:37) to afford the title compound (3.00 g, 57%) as a colourless oil.

¹H NMR 1.41 (s, 3H), 1.47 (s, 3H), 1.74 (s, 2H), 2.21 (m, 1H), 2.82 (d, 1), 3.06 (dd, 1H), 3.57 (dd, 1H), 3.73 (m, 2H), 3.93 (m, 3H), 4.15 (m, 1H), 7.02 (t, 1H), 7.19 (m, 2H), 7.26 (m, 1H); MS m/z 291

Method 5

3-Amino-1-[(2,2-dimethyl-1,3-dioxolan-4-yl)methyl]-3,4-dihydroquinolin-2(1H)-one

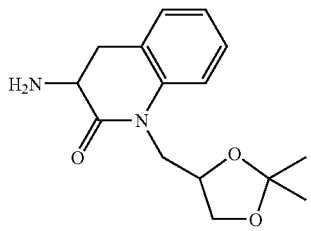

Sodium hydride (60% in oil, 191 mg, 4.70 mmol) was added to 3-amino-3,4-dihydroquinolin-2(1H)-one hydrochloride (*J. Med. Chem.*, 28, 1985; 1511–16, 450 mg, 2.27 mmol), in anhydrous DMF (6 mL) at 0° C. over a period of 5 min keeping the internal temperature at <10° C. The reaction was stirred for a further 30 min before addition of [2,2-dimethyl-1,3-dioxolan-4-yl]methyl methanesulfonate (*J. Med. Chem.* 35, 1992, 1650–62; 528 mg, 2.50 mmol) and the reaction has then heated to 80° C. for a period of 5 hours The reaction was then cooled and evaporated before addition of sat. aqueous NaHCO₃ (20 mL) and EtOAc (50 mL). The organic layer was then dried (MgSO₄), filtered and evaporated and the residue was purified by column chromatography (MeOH:DCM 1:19) to afford the title compound (330 mg, 53%) as colourless oil.

¹H NMR 1.33 (s, 3H), 1.40 (s, 1.5H), 1.45 (s, 1.5H), 1.96 (br. s, 2H), 2.89 (m, 1H), 3.07 (m, 1H), 3.60 (m, 1H), 3.82 (m 1.5H), 4.08 (m, 1.5H), 4.33 (m, 2H), 7.04 (m, 1H), 7.23 (m, 3H); MS m/z 277.

Method 6

N-[1-(3-{[tert-Butyl(dimethyl)silyl]oxy}-2-hydroxypropyl)-2-oxo-1,2,3,4-tetrahydroquinolin-3-yl]-5-chloro-1H-indole-2-carboxamide

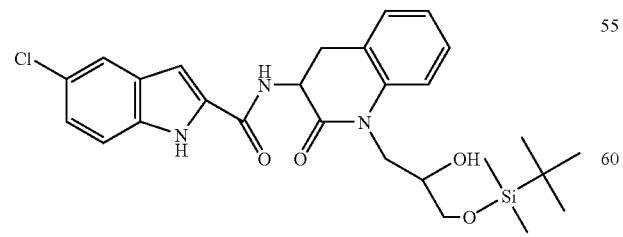

tert-Butylsilyldimethylsilyl trifluoromethane sulfonate (0.12 mL, 0.53 mmol), was added to a stirring suspension of 5-chloro-N-[1-(2,3-dihydroxypropyl)-2-oxo-1,2,3,4-tetrahydroquinolin-3-yl]-1H-indole-2-carboxamide (Example 39, 200 mg, 0.48 mmol) in DCM (5 mL) at 0° C. under argon. The reaction was stirred for 1 hour then quenched by addition of sat. aqueous NaHCO₃ (20 mL) and DCM (40 mL). The organic layer was then dried (MgSO₄), filtered, evaporated and purified by column chromatography to afford the title compound (84 mg, 33%) as a colourless oil.

¹H NMR 0.00 (m, 6H), 0.83 (2×s, 9H), 3.06 (m, 2H), 3.53 (m, 2H), 3.87 (m, 3H), 4.73 (m, 1.5H), 4.94 (d, 0.5H), 7.00 (t, 1H), 7.20 (m, 5H), 7.42 (d, 1H), 7.70 (s, 1H), 8.75 (d, 0.5H), 8.78 (d, 0.5H), 11.80 (s, 1H); MS m/z 528.

Method 7

5-Chloro-N-(1-{[(4R)-2,2-dimethyl-1,3-dioxolan-4-yl]methyl}-2-oxo-1,2,3,4-tetrahydroquinolin-3-yl)-1H-indole-2-carboxamide

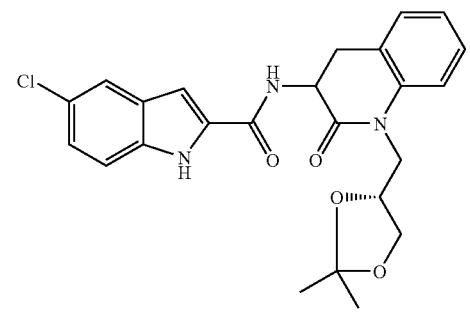

HOBT (209 mg, 1.55 mmol), 5-chloroindole-2-carboxylic acid (303 mg, 1.55 mmol), DIPEA (0.27 mL, 1.55 mmol) and then EDCI (370 mg, 1.94 mmol) were added to a solution of 3-amino-1-{[(4R)-2,2-dimethyl-1,3-dioxolan-4-yl]methyl}-3,4-dihydroquinolin-2(1H)-one (Method 8, 428 mg, 1.55 mmol) in DCM (10 mL). The reaction was stirred for 18 h at ambient temperature, diluted with EtOAc (20 mL), washed with 1 N NaOH (15 mL), 0.1 N HCl (15 mL), saturated aqueous NaHCO₃ solution (15 mL), dried (Na₂SO₄) and the volatiles removed under reduced pressure to give the title compound (684 mg, 97%) as a pale yellow solid.

¹H NMR 1.27 (m, 6H), 3.06 (m, 1H), 3.17 (app. t, 1H), 3.71 (m, 1H), 4.17 (m, 4H), 4.73 (m, 1H), 7.38 (m, 8H), 8.80 (d, 1H), 11.82 (s, 1H); MS m/z 476/478 (M+Na)

Method 8

3-amino-1-{[(4R)-2,2-dimethyl-1,3-dioxolan-4-yl]methyl}-3,4-dihydroquinolin-2(1H)-one

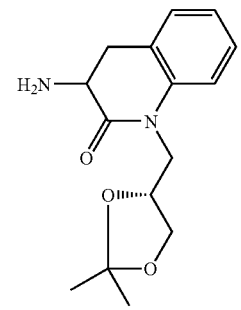

Prepared according to Method 5 using [(4S)-2,2-dimethyl-1,3-dioxolan-4-yl]methyl methanesulfonate (*J. Org. Chem*, 64, 1999 6782–6790) to give the title compound as a pale yellow oil.

¹H NMR (CDCl₃) 1.42 (m, 6H), 2.99 (m, 2H), 3.60 (m, 1H), 3.83 (m, 1.5H), 4.11 (m, 1.5H), 4.38 (m, 2H), 7.03 (m, 1H), 7.26 (d, 3H).

Method 9

N-[1-(2-Aminoethyl)-2-oxo-1,2,3,4-tetrahydroquinolin-3-yl]-5-chloro-1H-indole-2-carboxamide Trifluoroacetate

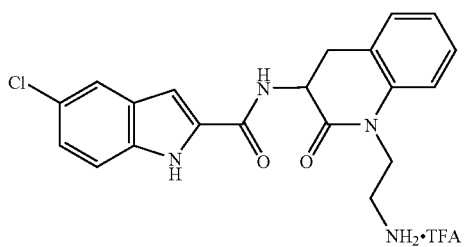

A solution of TFA:water (9:1, 4 mL) was added to tert-butyl{2-[3-{[(5-chloro-1H-indol-2-yl)carbonyl]amino}-2-oxo-3,4-dihydroquinolin-[(2H)-yl]ethyl}carbamate (Method 10, 1 g, 2.1 mmol) and the solution stirred at ambient temperature for 1 hours The reaction mixture was then azeotroped with toluene (3×10 mL) to give the title compound (0.957 g, 93%) as a tan solid.

¹H NMR 3.05 (m, 4H), 3.91 (m, 1H), 4.23 (m, 1H), 4.78 (m, 1H), 7.30 (m, 8H), 7.83 (br. s, 3H), 8.78 (d, 1H), 11.80 (s, 1H); MS m/z (M+Na) 405, 407.

Method 10 tert-butyl {2-[3-{[(5-chloro-1H-indol-2-yl)carbonyl]amino}-2-oxo-3,4-dihydroquinolin-1 (2H)-yl]ethyl}carbamate

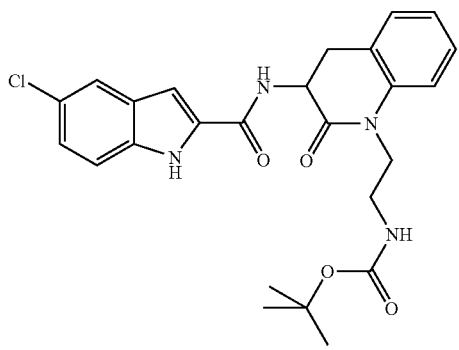

Prepared using an identical procedure as for Example 44 with sodium borohydride (1298 mg, 34.3 mmol), cobalt chloride hexahydrate (1632 mg, 6.86 mmol), tert-butyldicarbonate (1497 mg, 6.86 mmol) and 5-chloro-N-[1-(cyanomethyl)-2-oxo-1,2,3,4-tetrahydroquinolin-3-yl]-1H-indole-2-carboxamide (Method 11, 1299 mg, 3.43 mmol) in MeOH (15 mL) and THF (10 mL). The reaction was stirred at ambient temperature for 1.5 h to give the title compound (1560 mg, 94%) as a pale tan solid.

¹H NMR 1.47 (s, 6H), 3.13 (m, 4H), 3.93 (m, 2H), 4.78 (m, 1H), 7.25 (m, 7H), 7.75 (s, 1H), 8.85 (d, 1H), 11.87 (s, 1H); MS m/z (M+Na) 505, 507.

Method 11

5-Chloro-N-[1-(cyanomethyl)-2-oxo-1,2,3,4-tetrahydroquinolin-3-yl]-1H-indole-2-carboxamide

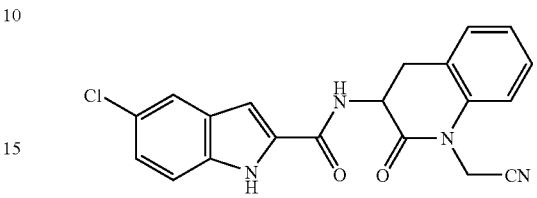

HOBT (168 mg, 1.24 mmol), 5-chloroindole-2-carboxylic acid (243 mg, 1.24 mmol), DIPEA (0.22 mL, 1.24 mmol) and then EDCI (296 mg, 1.55 mmol) were added to a solution of (3-amino-2-oxo-3,4-dihydroquinolin-1(2H)-yl)acetonitrile (Method 12, 250 mg, 1.24 mmol) in DCM (10 mL). The reaction was stirred for 18 h at ambient temperature, diluted with EtOAc (15 mL), washed with 1 N NaOH (15 mL), 1 N HCl (15 mL), saturated aqueous NaHCO₃ solution (15 mL), dried (MgSO₄) and the volatiles removed under reduced pressure to give the title compound (366 mg, 78%) as a tan solid.

¹H NMR 3.20 (m, 2H), 4.85 (m, 1H), 5.11 (s, 2H), 7.30 (m, 7H), 7.74 (s, 1H), 8.91 (d, 1H), 11.84 (s, 1H); MS m/z 377/379 (M–H)

Method 12

3-Amino-1-(2-cyanomethyl)-3,4-dihydroquinolin-2(1H)-one

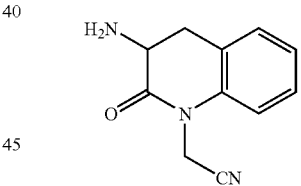

Sodium hydride (60% in oil, 2.74 g, 68.5 mmol) was added to 3-amino-3,4-dihydroquinolin-2(1H)-one hydrochloride (*J. Med. Chem.*, 28, 1985; 1511–16, 6.47 g, 32.6 mmol) in anhydrous DMF (70 mL) at 0° C. over a period of 5 min. After 1 hour the mixture was warmed to ambient temperature, stirred for 2 hours then cooled in an ice bath before bromoacetonitrile (2.28 mL, 32.68 mmol) was added. The mixture was again warmed to ambient temperature and stirred for 18 hours. The reaction was diluted with EtOAc (100 mL) and washed with sat. aqueous K₂CO₃ (20 mL). The aqueous was extracted with DCM:MeOH (19:1) (3×50 mL) and the combined organics dried (Na₂SO₄), filtered and evaporated. The residue was purified by column chromatography (DCM to DCM:MeOH (9:1)) to afford the title compound (5.28 g, 81%) as a brown oil.

¹H NMR (CDCl₃) 1.79 (br. s, 2H), 2.90 (app. t, 1H), 3.11 (dd, 1H), 3.65 (dd, 1H), 4.68 (d, 1H), 5.03 (d, 1H), 7.05 (d, 1H), 7.13 (t, 1H), 7.25 (d, 1H), 7.35 (t, 1H); MS m/z 202.

Method 13

N-[1-(3-{[tert-Butyl(dimethyl)silyl]oxy}propyl)-2-oxo-1,2,3,4-tetrahydroquinolin-3-yl]-5-chloro-1H-indole-2-carboxamide

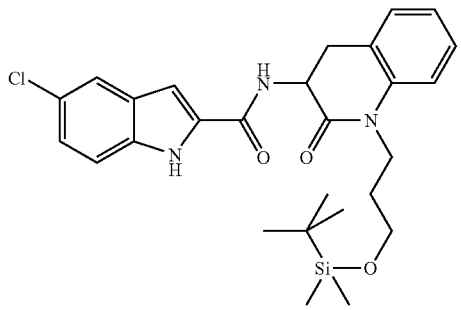

Prepared exactly as in Method 7 using HOBT (174 mg, 1.3 mmol), 5-chloroindole-2-carboxylic acid (250 mg, 1.3 mmol), DIPEA (0.22 mL, 1.3 mmol), EDCI (308 mg, 1.6 mmol) and 3-amino-1-(3-{[tert-butyl(dimethyl)silyl]oxy}propyl)-3,4-dihydroquinolin-2(1H)-one (Method 14, 432 mg, 1.3 mmol) in DCM (10 mL). This gave the title compound (548 mg, 82%) as a pale yellow solid.

$^1$H NMR 0.00 (2×s, 6H), 0.85 (s, 9H), 1.73 (m, 2H), 3.07 (m, 2H), 3.63 (m, 2H), 3.95 (br. t, 2H), 4.70 (m, 1H), 7.12 (m, 6H), 7.40 (d, 1H), 7.70 (s, 1H), 8.78 (d, 1H), 11.80 (s, 1H), MS m/z 534/536 (M+Na)

Method 14

3-Amino-1(3-{[tert(dimethyl)silyl]oxy}propyl)-3,4-dihydroquinolin-2(1H)-one

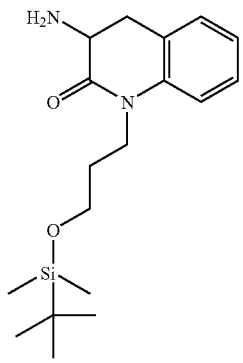

The title compound was prepared in an analogous method to Method 1 using (3-bromopropoxy)(tert-butyl)dimethylsilane as elecrophile.

$^1$H NMR 0.00 (s, 6H), 0.88 (s, 9H), 1.75 (s, 2H), 1.83 (m, 2H), 2.74 (d, 1H), 3.00 (dd, 1H), 3.48 (dd, 1H), 3.66 (m, 2H), 3.98 (m, 2H), 6.96 (t, 1H), 7.16 (m, 3H); MS m/z 335

What is claimed is:

1. A compound of formula (1):

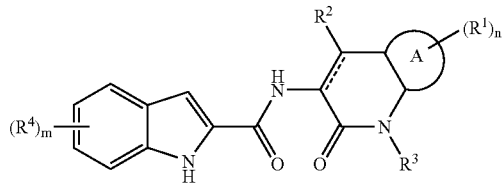

wherein

----- is a single bond;

A is phenylene;

n is 1;

R$^1$ is hydrogen;

R$^2$ is hydrogen;

R$^3$ is selected from C$_{1-4}$alkyl optionally substituted by 1 or 2 hydroxy groups provided that when there are 2 hydroxy groups they are not substituents on the same carbon, cyanoC$_{1-4}$alkyl, and C$_{1-4}$alkyl substituted by 1 or 2 R$^8$ groups provided that when there are 2 R$^8$ groups they are not substituents on the same carbon;

R$^8$ is independently selected from hydroxy, heterocyclyl, C$_{1-4}$alkanoyl, C$_{1-4}$alkoxy, C$_{1-4}$alkanesulfinyl, C$_{1-4}$alkanesulfonyl, —COCOOR$^9$, (R$^9$)(R$^{10}$)NCO—, —COCH$_2$OR$^{11}$, (R$^9$)(R$^{10}$)N—, —COOR$^9$ and 2,2-dimethyl-1,3-dioxolan-4-yl;

R$^9$ and R$^{10}$ are independently selected from hydrogen, hydroxy, C$_{1-4}$alkyl optionally substituted by 1 or 2 hydroxy groups provided that when there are 2 hydroxy groups they are not substituents on the same carbon and C$_{1-4}$alkyl substituted by C$_{1-4}$alkoxy and wherein R$^9$ and R$^{10}$ can together with the nitrogen to which they are attached form 4- to 6-membered ring where the ring is optionally substituted on carbon by 1 or 2 substituents selected from hydroxy or carboxy;

R$^{11}$ is selected from hydrogen, C$_{1-4}$alkyl, C$_{1-4}$alkoxy and hydroxyC$_{1-4}$alkyl;

m is 1;

R$^4$ is chloro;

or a pharmaceutically acceptable salt or prodrug thereof.

2. A compound of claim 1 selected from:

5-chloro-N-[1-(methoxycarbonylmethyl)-2-oxo-1,2,3,4-tetrahydroquinolin-3-yl]-1H-indole-2-carboxamide;

N-[1-(carboxymethyl)-2-oxo-1,2,3,4-tetrahydroquinolin-3-yl]-5-chloroindole-2-carboxamide; and 5-chloro-N-(2-oxo-1,2,3,4-tetrahydroquinolin-3-yl)-1H-indole-2-carboxamide;

or a pharmaceutically acceptable salt or an in-vivo hydrolysable ester thereof.

3. A pharmaceutical composition which comprises a compound of claim 1, or a pharmaceutically acceptable salt or in-vivo hydrolysable ester thereof, in association with a pharmaceutically acceptable diluent or carrier.

4. A process for the preparation of a compound claim 1, which process comprises:

reacting an acid of the formula (2)

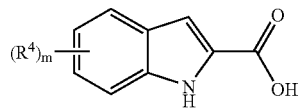

(2)

or an activated derivative thereof; with an amine of formula (3)

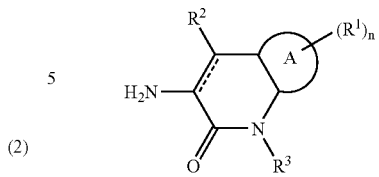

(3)

and thereafter if necessary
 i) converting a compound of the formula (1) into another compound of the formula (1);
 ii) removing any protecting groups; or
 iii) forming a pharmaceutically acceptable salt or in vivo hydrolysable ester.

* * * * *